United States Patent
Takeuchi et al.

(10) Patent No.: US 7,420,684 B2
(45) Date of Patent: Sep. 2, 2008

(54) METHOD AND APPARATUS FOR MEASURING SURFACE CARRIER RECOMBINATION VELOCITY AND SURFACE FERMI LEVEL

(75) Inventors: Hideo Takeuchi, Tokyo (JP); Yoshitsugu Yamamoto, Tokyo (JP)

(73) Assignee: Mitsubishi Denki Kabushiki Kaisha, Tokyo (JP)

( * ) Notice: Subject to any disclaimer, the term of this patent is extended or adjusted under 35 U.S.C. 154(b) by 184 days.

(21) Appl. No.: 11/256,180

(22) Filed: Oct. 24, 2005

(65) Prior Publication Data

US 2006/0094133 A1  May 4, 2006

(30) Foreign Application Priority Data

Oct. 29, 2004  (JP)  ............................. 2004-316818

(51) Int. Cl.
*G01N 21/00* (2006.01)
*G01N 21/55* (2006.01)

(52) U.S. Cl. ........................................ 356/445; 356/432

(58) Field of Classification Search ................ 356/432, 356/445

See application file for complete search history.

(56) References Cited

U.S. PATENT DOCUMENTS 5,255,070 A  10/1993  Pollak et al.
5,260,772 A  11/1993  Pollak et al.
5,287,169 A * 2/1994  Pollak et al. ................ 356/445
2005/0099623 A1  5/2005  Takeuchi et al.

FOREIGN PATENT DOCUMENTS

JP  2002-340675  11/2002

OTHER PUBLICATIONS

V. L. Alperovich, A. G. Paulish, and A. S. Terekhov,"Domination of adatom-induced over defect-induced surface states on p-type GaAs (Cs,O) at room temperature," Phys. Rev. B 50, 5480 (1994). [ISI].*
Hideo Takeuchi, Toshitaka Kamo, Yoshitsugu Yamamoto, Tomoki Oku, "Photovoltaic effects on Franz-Keldysh oscillations in photoreflectance spectra," J. Appl. Phys. 97, 063708 (2005).*
C. Wetzel, T. Takeuchi, H. Amano, and I. Akasaki, "Piezoelectric Franz-Keldysh effect in strained GaIn/GaN heterostructures," J. Appl. Phys. 85, 3786 (1999). [ISI].*
Pearson, Ben and Paul Shearer, "Franz-Keldysh Effect," University of Minnesota, http://mxp.physics.umn.edu/s05/Projects/S05Franz/, May 10, 2005.*

(Continued)

*Primary Examiner*—Gregory J. Toatley, Jr.
*Assistant Examiner*—Rebecca C Slomski
(74) *Attorney, Agent, or Firm*—Leydig, Voit & Mayer, Ltd.

(57) ABSTRACT

A pump beam irradiates the surface of a semiconductor sample through modulator while irradiating the surface with a probe beam so that a detector measures a light-modulated spectrum of the probe beam reflected from the surface of the semiconductor sample. Then, surface electric field strength is calculated from the period of Franz-Keldysh oscillations appearing in the light-modulated spectrum, and the surface recombination velocity and surface Fermi level are calculated based on a relation between the surface electric field strength and the probe beam power density.

4 Claims, 20 Drawing Sheets

OTHER PUBLICATIONS

Paget D, Bonnet J E, Berkovits V L, Chiaradia P and Alvila J "Sulfide-passivated GaAs (001). II. Electronic properties" 1996 Phys. Rev. B 53 4604 pp. 4615-4622.*

Shen, H. et al.; "Franz-Keldysh oscillations in modulation spectroscopy", *J. Appl. Phys.*, vol. 78, No. 4, pp. 2151-2120, (Aug. 15, 1995).

Shen, H. et al.; "Photoreflectance study of surface Fermi level in GaAs and GaAlAs", *Appl. Phys. Lett.*, vol. 57, No. 20, pp. 2118-2120, (Nov. 12, 1990).

Hoffman, C. A. et al.; "Study of surface recombination in GaAs and InP by picosecond optical techniques", *J. Appl. Phys.*, vol. 51, No. 3, pp. 1603-1604, (Mar. 1980).

* cited by examiner

METHOD AND APPARATUS FOR MEASURING SURFACE CARRIER RECOMBINATION VELOCITY AND SURFACE FERMI LEVEL

BACKGROUND OF THE INVENTION

1. Field of the Invention

This invention relates to a method and apparatus for measuring surface carrier recombination velocity and surface Fermi level, and particularly to a method and apparatus for evaluating the carrier recombination velocity and the surface Fermi level at a semiconductor surface precisely at the same time in a non-destructive and contactless manner using modulation spectroscopy belonging to spectroscopic measurement technology.

2. Description of the Related Art

In general, the characteristics and reliability of semiconductor devices are closely related to surface and interface states of the epitaxial (herein below abbreviated as "epi") layer structures. The term "semiconductor" means all kinds of solid materials the carrier concentration of which can be controlled by a doping technique. Further, when being referred to simply as "surface" hereinafter, it also includes the meaning of "interface." For example, the surface/interface states affect a reduction in reliability, an increase in noise, frequency dispersion, and breakdown voltage in field effect transistors (FETs). They also increase a recombination current in heterojunction bipolar transistors.

In a surface-emitting laser diode (LD), a threshold current and differential quantum efficiency are related to the surface state. For these reasons, the quantitative evaluation of surface states is considered to be a key to the development and mass production of high-performance and high-reliability devices.

Photoreflectance (hereinbelow abbreviated as PR) spectroscopy is a kind of non-destructive, contactless spectroscopy based on modulation techniques and has recently been attracting attention as optical evaluation techniques for semiconductor surfaces (for example, see Japanese patent laid-open application No. 2002-340675). One of the reasons arises from the fact that PR spectroscopy is sensitive to the electric field strength. For example, in the spectrum of a semiconductor sample having a built-in electric field obtained by PR modulation spectroscopy, an oscillation pattern, called a Franz-Keldysh (hereinbelow abbreviated as FK) oscillation, appears near the critical point of the optical transition energy.

Electro-optic energy corresponding to a period of FK oscillations is determined by the surface electric field strength. In particular, since the surface electric field of the semiconductor is generated by a phenomenon called "surface Fermi level pinning", the measurement of FK oscillations can be considered as one of the methods for estimating surface Fermi level. For example, as a practical matter, Shen et al. measured the PR spectrum of an epi structure consisting of an undoped $Al_xGa_{1-x}A_S$ (i-$Al_xGa_{1-x}A_S$) layer, an n-type $Al_xGa_{1-x}As$ (n-$Al_xGa_{1-x}As$) layer, and an n-type substrate to obtain the Fermi level of the i-$Al_xGa_{1-x}As$ layer. See Appl. Phys. Lett. 57, 2118 (1990).

The parameter, the so-called surface recombination velocity, is another important parameter that characterizes the semiconductor surface. This is a parameter that characterizes the recombination of carriers at the surface, and it affects the performance of the semiconductor device much as the surface Fermi level does.

Measurement methods other than the above-mentioned PR spectroscopy have been used to evaluate the surface recombination velocity. For example, there is a widespread method of performing time-resolved measurements on photoluminescence (hereinbelow abbreviated as PL) from the semiconductor and analyzing the decay profile of PL intensity plotted as a function of time after optical excitation to determine the surface recombination velocity.

In order to evaluate the surface Fermi level from the FK oscillations by a conventional measurement method, it has been considered necessary to eliminate a photovoltaic effect caused by continuous probe beam irradiation because the photovoltaic effect reduces the surface electric field strength. In order to suppress the photovoltaic effect, for example, in the above-mentioned measurement method proposed by Shen et al., the probe beam is defocused on the sample surface so that the density of the probe beam power is 0.1 $\mu W/cm^2$ or less. Such a very weak probe beam, needless to say, causes a signal-to-noise (S/N) ratio reduction, resulting in difficulty in the PR measurement.

On the other hand, there are also problems in the method of evaluating the surface recombination velocity. One of the problems originates from the fact that in the analysis of the decay profile, it is difficult to separate the surface carrier recombination velocity from the carrier recombination in a semiconductor crystal. Such a method based on PL spectroscopy, of course, is inapplicable to measure the materials whose PL intensity is weak.

Since both of the above-mentioned two parameters, surface Fermi level and surface recombination velocity, reflect the surface state, it is considered that they correlate with each other. However, as mentioned above, the Fermi level and the surface recombination velocity have been conventionally measured by completely different methods. This means that the values of the Fermi level and the surface recombination velocity are obtained under different measurement conditions. Therefore, there is a fundamental problem that the discussion on a correlation between the two parameters acompanies with uncertainty resulting from the difference in the measurement. It is evident that two different kinds of measurements are needed to evaluate the two parameters. This results in an increase in evaluation time and cost, which prevents the precise surface design of semiconductor devices.

The present invention has been made to solve the above-mentioned problems. It is a purpose of the present invention to provide a modulation spectroscopic measurement and analysis method, which can determine not only the surface Fermi level but also the surface recombination velocity even from FK oscillations affected by a relatively high-power probe beam. It is another purpose of the present invention to provide an apparatus suitable for this method and a sample structure suitable to be evaluated.

SUMMARY OF THE INVENTION

According to one aspect of the present invention, in a method of measuring surface carrier recombination velocity and surface Fermi level of a semiconductor sample, a pump beam is irradiated onto a semiconductor while irradiating a probe beam onto the semiconductor sample and a PR spectrum of the probe beam reflected from the surface of the semiconductor sample is measured. Then, the surface electric field strength is calculated from the period of Franz-Keldysh oscillations appearing in the PR spectrum, and the surface recombination velocity and surface Fermi level are calculated from the surface electric field strength plotted as a function of the probe beam power density.

According to the present invention, the measurement method for surface carrier recombination velocity is configured as mentioned above, so that both the surface recombination velocity and the surface Fermi level can be obtained or estimated at the same time from FK oscillations appearing in the PR spectrum in a non-destructive and contactless manner.

DESCRIPTION OF THE PREFERRED EMBODIMENTS

A preferred embodiment of the present invention will now be described with reference to the accompanying drawings. In the description of this embodiment, an analysis method and a measurement method for allowing the analysis will first be described. Note here that the analysis method is applicable to calculate both the surface recombination velocity and the surface Fermi level at the same time from FK oscillations appearing in spectra (for example, PR spectra, modulated transmission spectra, or modulated absorption spectra) obtained by a modulation spectroscopic measurement technique. Next, the details of the appropriateness and effectiveness of the analysis method will be described. Subsequently, an embodiment of the structure of an apparatus suitable for the measurement and analysis method will be described. Following this, an epi structure whose surface recombination velocity and surface Fermi level are precisely measured will be illustrated with a detailed description of the effects of the structure. Finally, a specific example will be illustrated to verify the possibility of carrying out this invention.

The following descriptions indicate a measurement and analysis method for extracting surface recombination velocity and surface Fermi level at the same time from FK oscillations appearing in PR spectra. Note that, although the PR spectra are taken by way of example to describe the embodiment, the same measurement and analysis method can be applied to a modulated transmission spectra or a modulated absorption spectra to extract surface recombination velocity and surface Fermi level at the same time.

Figure 1:
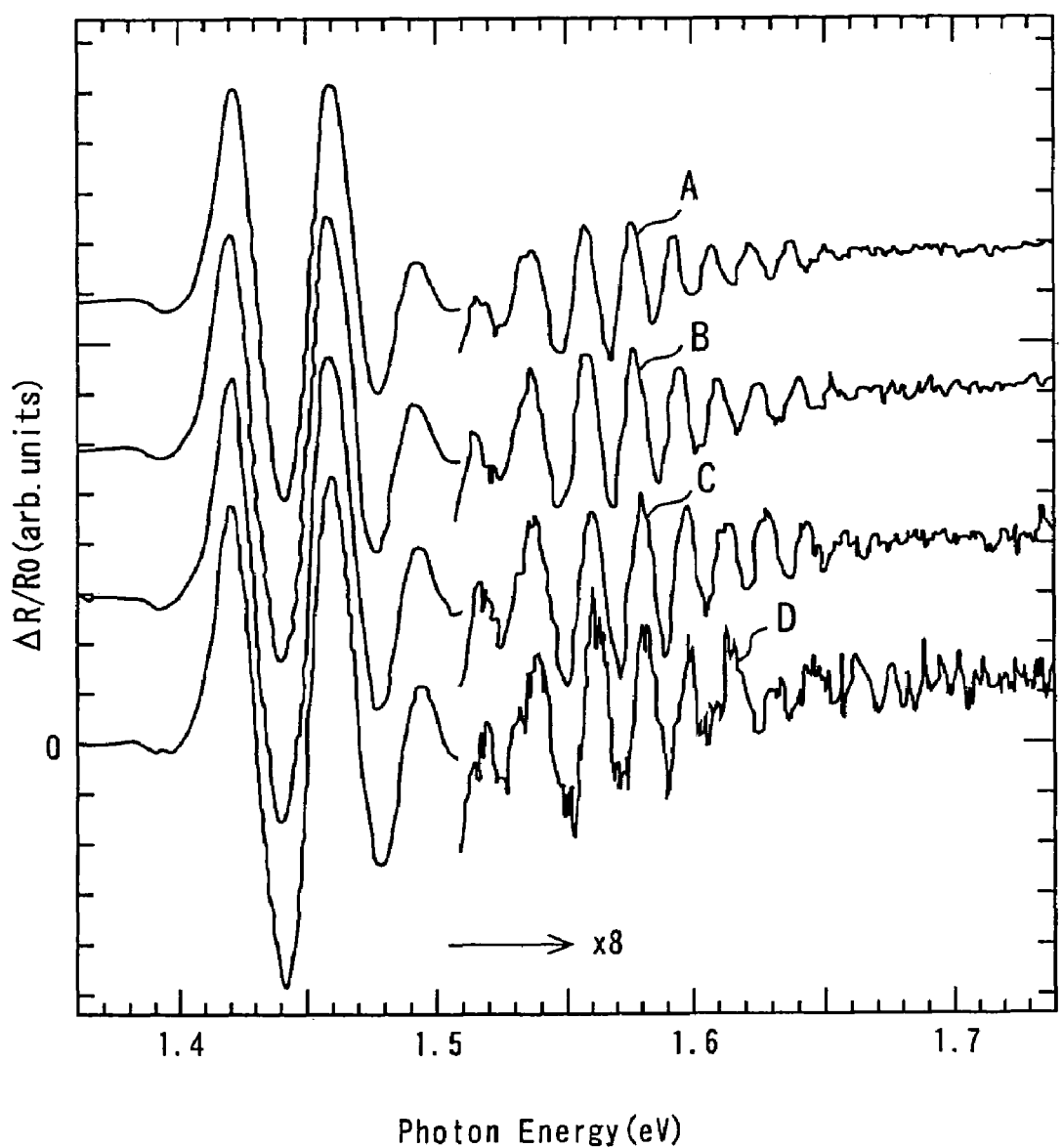
FIG. 1 shows examples of PR spectra at various probe beams.

(1) PR spectra at various probe beam power densities are measured. FIG. 1 shows examples of spectra obtained. FIG. 1 plots photon energy on the abscissa and PR signal intensity on the ordinate. In FIG. 1, spectrum A represents a case where the probe beam power density is 30 $\mu W/cm^2$, spectrum B represents a case where it is 13 $\mu W/cm^2$, spectrum C represents a case where it is 5.5 $\mu W/cm^2$, and spectrum D represents a case where it is 2.8 $\mu W/cm^2$.

Figure 2:
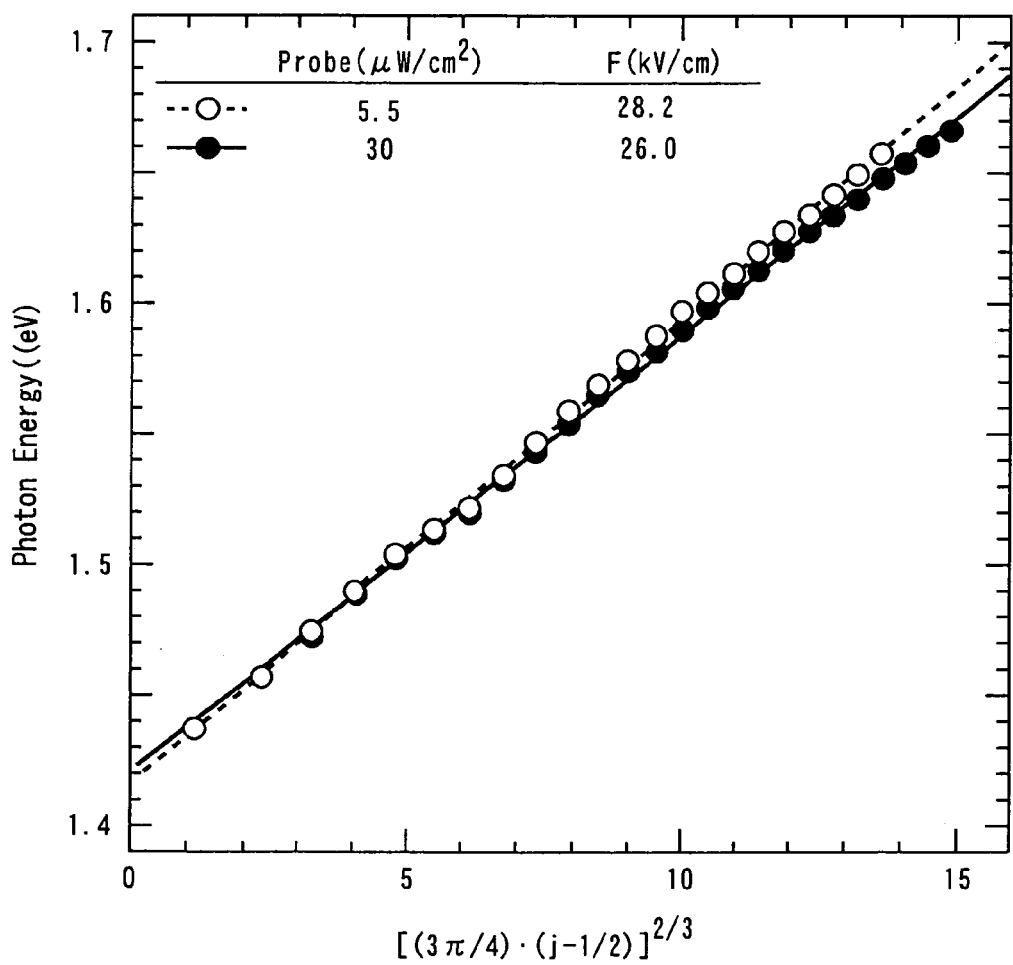
FIG. 2 shows plotted extrema in each of FK oscillation patterns in PR spectra.
Figure 3:
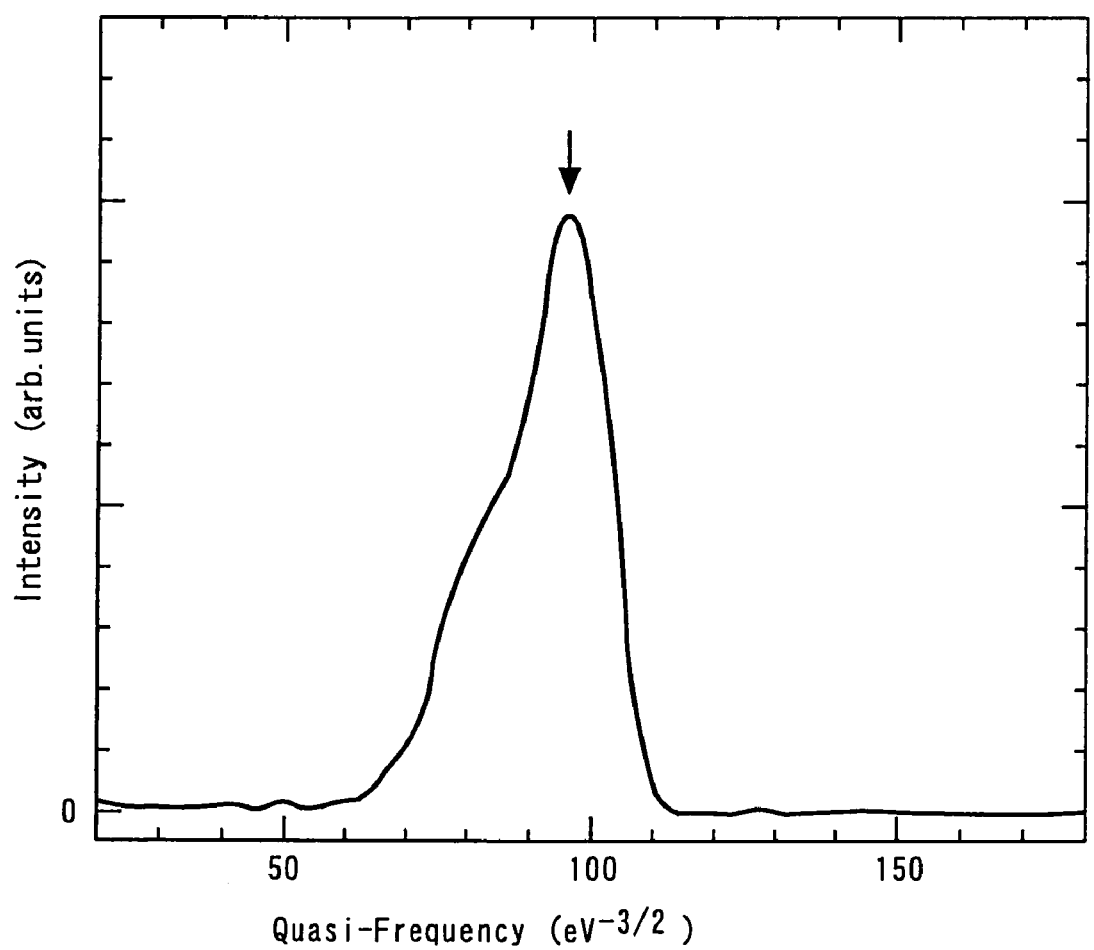
FIG. 3 shows the Fourier-transformed spectrum of the FK oscillation pattern at the probe beam power density of 30 $\mu W/cm^2$.

(2) A period of FK oscillations appearing in each PR spectrum (corresponding to electro-optic energy) is analyzed to calculate surface electric-field strength. FIG. 2 shows plotted extrema in each of oscillation patterns analyzed from FK oscillation analysis at the probe beam power densities of 30 $\mu W/cm^2$ and 5.5 $\mu W/cm^2$, respectively. FIG. 3 shows the Fourier-transformed spectrum of the FK oscillation at the probe beam power density of 30 $\mu W/cm^2$. The calculation procedure of the surface electric field strength will be described later.

Figure 4:
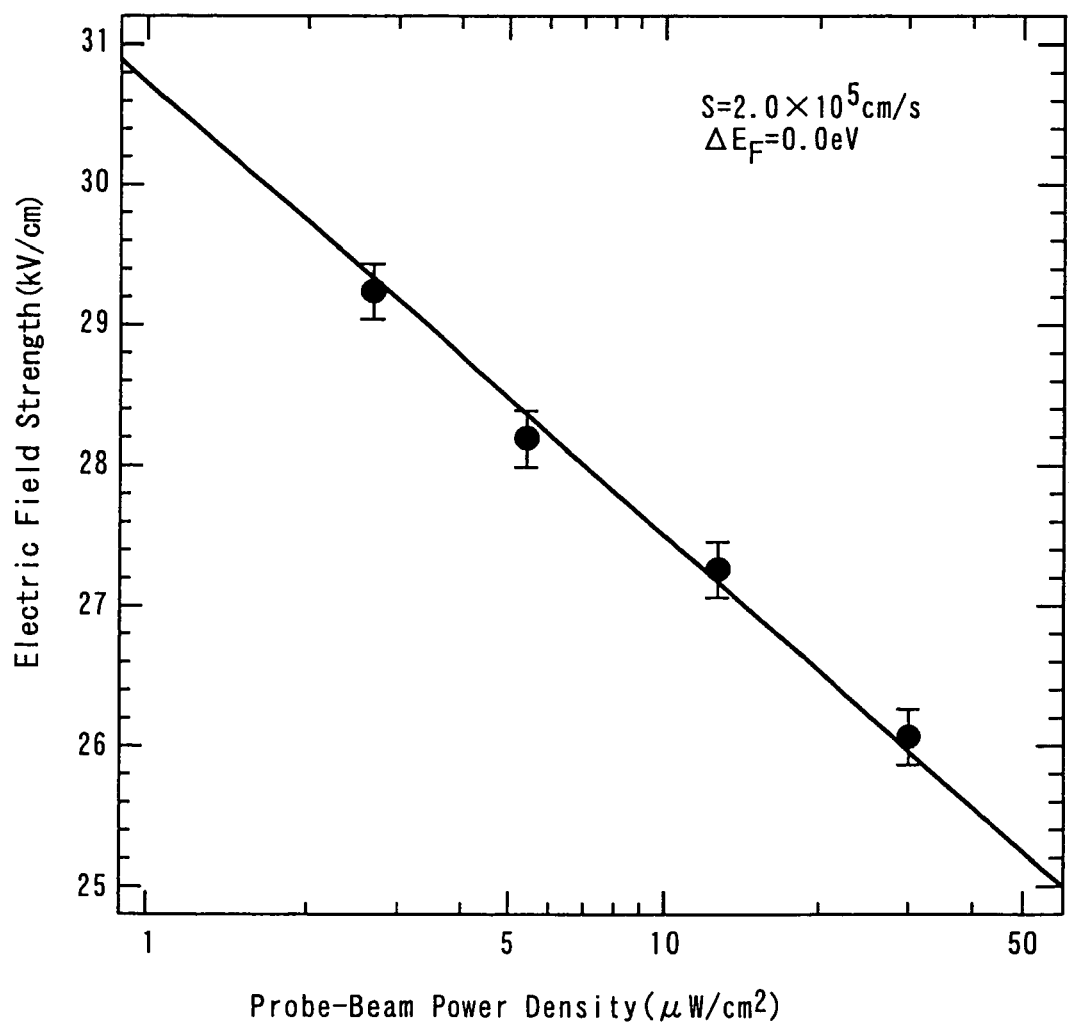
FIG. 4 shows the surface electric field strength plotted as a function of probe beam power density.

(3) The surface electric field strength obtained is plotted as a function of the probe beam power density to perform fitting with the parameters of the surface recombination velocity and surface Fermi level using a simulator. FIG. 4 shows an example of fitting. In FIG. 4, solid or filled circles represent experimental values, and the solid line represents a plot of calculated values. Further, S represents the surface recombination velocity and $\Delta E_F$ represents the surface Fermi level.

As will be described later, the surface electric field strength is strongly dependent on these two parameters. The other parameters, such as carrier lifetime (carrier bulk lifetime) in a semiconductor crystal, do not affect the fitting. Thus the surface recombination velocity and the surface Fermi level can be determined precisely.

Figure 5:
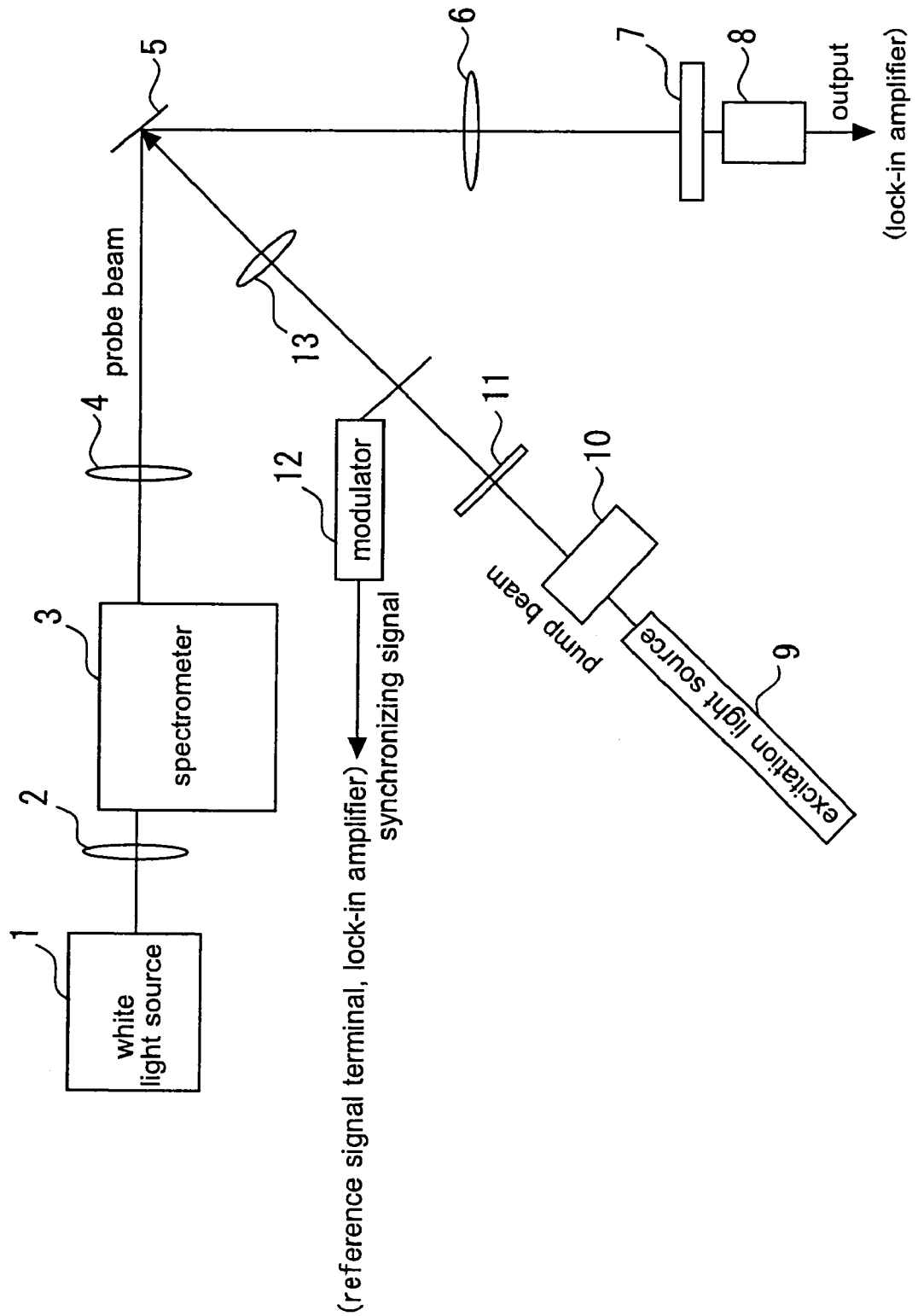
FIG. 5 is a schematic diagram showing the structure of a PR measurement apparatus.

The following descriptions indicate the details of the measurement and analysis methods. FIG. 5 is a schematic diagram showing the structure of a PR measurement apparatus. A PR spectrum is measured using this apparatus according to the following procedure:

(1) A beam of light, e.g., a laser pump beam, is emitted from an excitation light source 9, passed through an exciting light power stabilizer 10 and an exciting light filter 11, converted by a modulator (e.g., chopper) 12 from continuous light to chopped light, and directed onto a semiconductor sample 5 through a pump beam condenser lens 13.

(2) The external modulated beam scattered on the sample 5 is guided to a PR signal detector 8 through a reflective probe-beam condenser lens 6 and a long pass filter 7. The phase of a lock-in amplifier, not shown here, is adjusted to that of a signal detected in the above state. The phase adjustment is made according to the following procedure:

First, under a condition where the long pass filter 7 is removed, the pump beam scattered on the sample 5 is condensed onto the PR signal detector 8 through a lens 6. After current-voltage conversion or voltage amplification of the PR signal from the detector 8 are performed, the electrical signal obtained is sent to the lock-in amplifier as a reference signal so that the lock-in amplifier will be adjusted to be in phase with the reference signal.

(3) After the phase adjustment, the long pass filter 7 is inserted so that the pump beam scattered on the surface of the sample 5 will not enter the PR signal detector 8.

(4) In order to measure a PR spectrum of the sample 5, light from a white light source (e.g., lamp) 1 is guided into a spectrometer 3 through a white light condenser lens 2. The light beam emitted from the spectrometer 3 and passed through a probe beam condenser lens 4 is a probe beam.

(5) The spectrometer 3 is swept across the spectrum and then the PR signal detector detects the probe beam.

(6) The detected signal is passed through a band pass filter, not shown here, to divide it into a direct current (DC) component corresponding to reflectance R and an alternative current (AC) component corresponding to modulated reflectance ΔR.

(7) The DC component and the AC component are measured by a DC voltmeter and the lock-in amplifier, respectively.

(8) The quantity ΔR/R is calculated on a computer to obtain a PR signal.

(9) The steps (5) to (8) are repeated to record ΔR/R spectra as a function of wavelength λ or photon energy.

The following descriptions indicate the analysis method for FK oscillations appearing in the spectra obtained. As one of the techniques for calculating the surface electric field strength from FK oscillations, there is a method of plotting the extrema in each of oscillation patterns as shown in FIG. 2 to determine the surface electric field strength from the slope. In FIG. 2, open circles represent the extrema at the probe beam power density of 5.5 μW/cm$^2$, and closed circles represent the extrema at the probe beam power density of 30 μW/cm$^2$.

Figure 6:
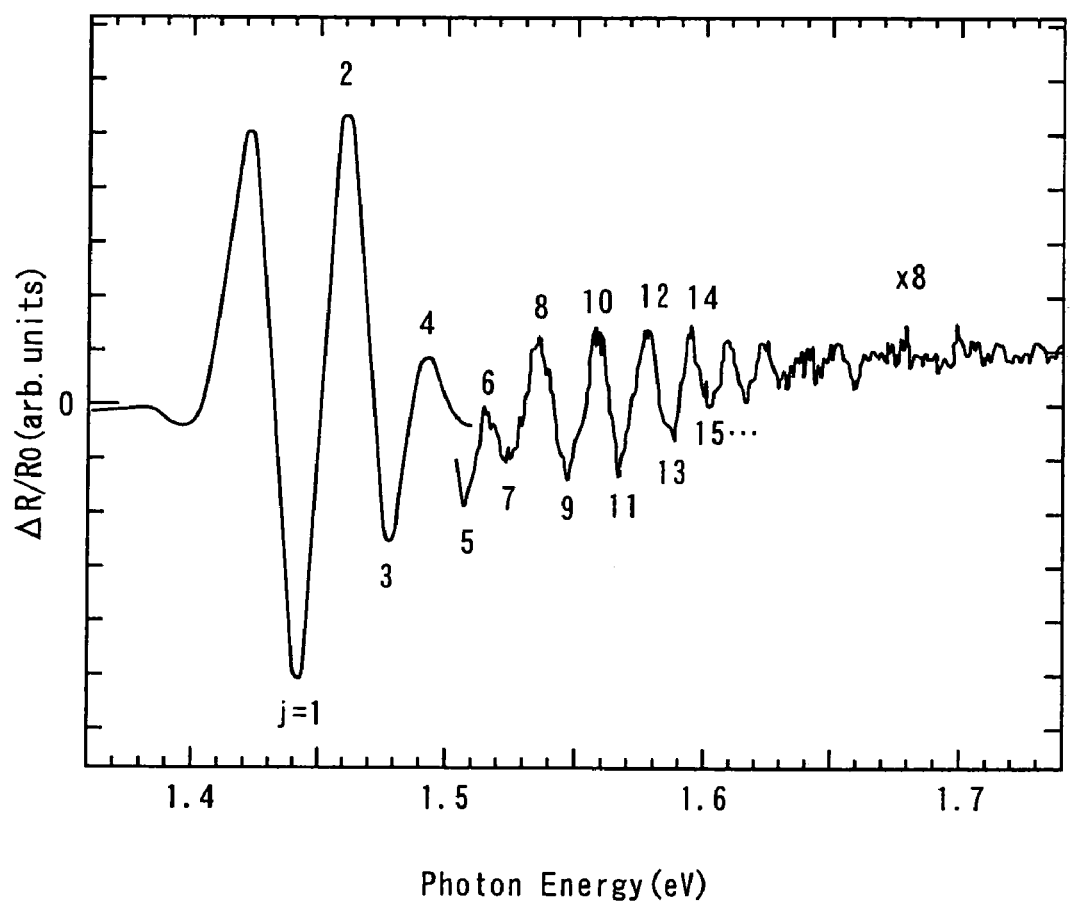
FIG. 6 shows an example of the assignment of index j to the extrema in the FK oscillations.

In this method, index j is assigned to the extrema in the FK oscillations as shown in FIG. 6. Next, the indexed extrema are plotted as a function of quasi-index Xj determined by the index j. The relation between each extremum and Xj depends on the distribution of an built-in electric field in the measured sample and the modulation method. For example, when the sample is composed of two undoped/doped layers, the electric field strength in the undoped layer is approximately uniform. In such a case, when the modulation is so strong that the surface electric field can be neglected, the relation between the extremum and Xj is represented by the following equations:

[Eq. 1]

$$\hbar\omega_j = \hbar\Theta X_j + E_{g,0} \quad (1a)$$

-continued $$(\hbar\Theta)^3 = \frac{e^2\hbar^2 F^2}{2\mu} \quad (1b)$$

where $\hbar\omega_j$, $\hbar\Theta$, and $E_{g,0}$ are the photon energy of the jth extremum, the electro-optic energy, and the band-gap energy of the sample, respectively. Xj in Equation (1a) is represented by the following equation:

[Eq. 2]

$$X_j = \left[\frac{3\pi}{4}\left(j - \frac{\phi}{\pi}\right)\right]^{2/3} \quad (2)$$

where φ is a phase factor whose general expression is represented by the following equation. Note that the general expression is also applicable to the case where a protective film is formed on the surface of which electric field causes FK oscillations.

[Eq. 3]

$$\phi = \frac{\pi}{2} + \delta(\hbar\omega_j) \quad (3)$$

where $\delta(\hbar\omega_j)$ is a physical quantity, called a phase delay, related to interference of probe beam inside the protective film, and is given by the following equation using the thickness $d_m$ of the mth film and the wave number $k_m$ of the beam with an energy of $\hbar\omega_j$:

[Eq. 4]

$$\delta(\hbar\omega) = 2\sum_{m=1}^{N} k_m(\hbar\omega)d_m \quad (4)$$

For calculating the electric field strength, there is a method of applying Fourier-transform to the PR spectrum in order to obtain a spectrum as shown in FIG. 3 that enables to calculate the electric field strength from the peak position. Before the Fourier transform, the PR spectrum measured as a function of photon energy is usually converted by variable $\xi=(\hbar\omega-E_{g,0})^{3/2}$. The Fourier transform is performed according to the following equation:

[Eq. 5]

$$|(\nu)| = \left|\int_0^\infty \frac{\Delta R(\xi)}{R}\exp(-2\pi i\nu\xi)d\xi\right|^2 \quad (5)$$

In order to calculate the electric field strength from the peak position $\nu_{max}$ of the spectrum obtained by the Fourier transform, the following equation is used:

[Eq. 6]

$$v_{max} = \frac{2}{3\pi} \frac{\sqrt{2\mu_r}}{e\hbar F} \quad (6)$$

where $\mu_r$ is the reduced effective mass of an electron-hole pair.

The following descriptions indicate a fitting technique for extracting the surface Fermi level and the surface recombination velocity from the surface electric field strengths plotted as a function of probe beam power density as shown in FIG. 4. In order to show the principle of fitting and hence proof of its appropriateness and effectiveness, the following descriptions assume the case where the sample 5 has the i-GaAs/n-GaAs structure. Specific values for the sample structure are as follows: i-GaAs layer thickness of 200 nm, n-GaAs layer thickness of 1.0 μm, and n-GaAs layer doping concentration of $3\times10^{18}$ cm$^{-3}$. The other parameters used for this simulation have values shown in Tables 1 and 2, unless otherwise noted. Table 1 lists parameters used for calculating the built-in electric field strength and carrier density in the epitaxial layer structure of i-GaAs (200 nm thick) and n-GaAs (1.0 μm thick at the doping concentration of $3\times10^{18}$ cm$^{-3}$). In Table 1, the parameters have common values between the i-GaAs layer and the n-GaAs layer. Table 2 lists parameters having different values between the i-GaAs layer and the n-GaAs layer. Note that the doping density denotes the density of an ionized dopant.

TABLE 1

| Parameter | Value |
| --- | --- |
| Temperature (K) | 300 |
| Photon Energy of Probe Beam (eV) | 1.5 |
| Dielectric Constant | 13.18 |
| Refractive Index | 3.666 |
| Absorption Coefficient (cm$^{-1}$) | 9300 |
| Electron Density-of-State Mass (Free Electron Mass Units) | 0.067 |
| Hole Density-of-State Mass (Free Electron Mass Units) | 0.547 |
| Intrinsic Carrier Concentration ($\times 10^6$ cm$^{-3}$) | 2.1 |

TABLE 2

| | Value | |
| --- | --- | --- |
| Parameter | i-GaAs Layer | n-GaAs Layer |
| Band-Gap Energy (eV) | 1.424 | 1.345 |
| Electron Mobility (cm$^2$/Vs) | 8000 | 2100 |
| Hole Mobility (cm$^2$/Vs) | 400 | 90 |
| Electron Carrier Bulk Lifetime (ns) | 50 | 50 |
| Hole Carrier Bulk Lifetime (ns) | 50 | 5 |

Figure 7:
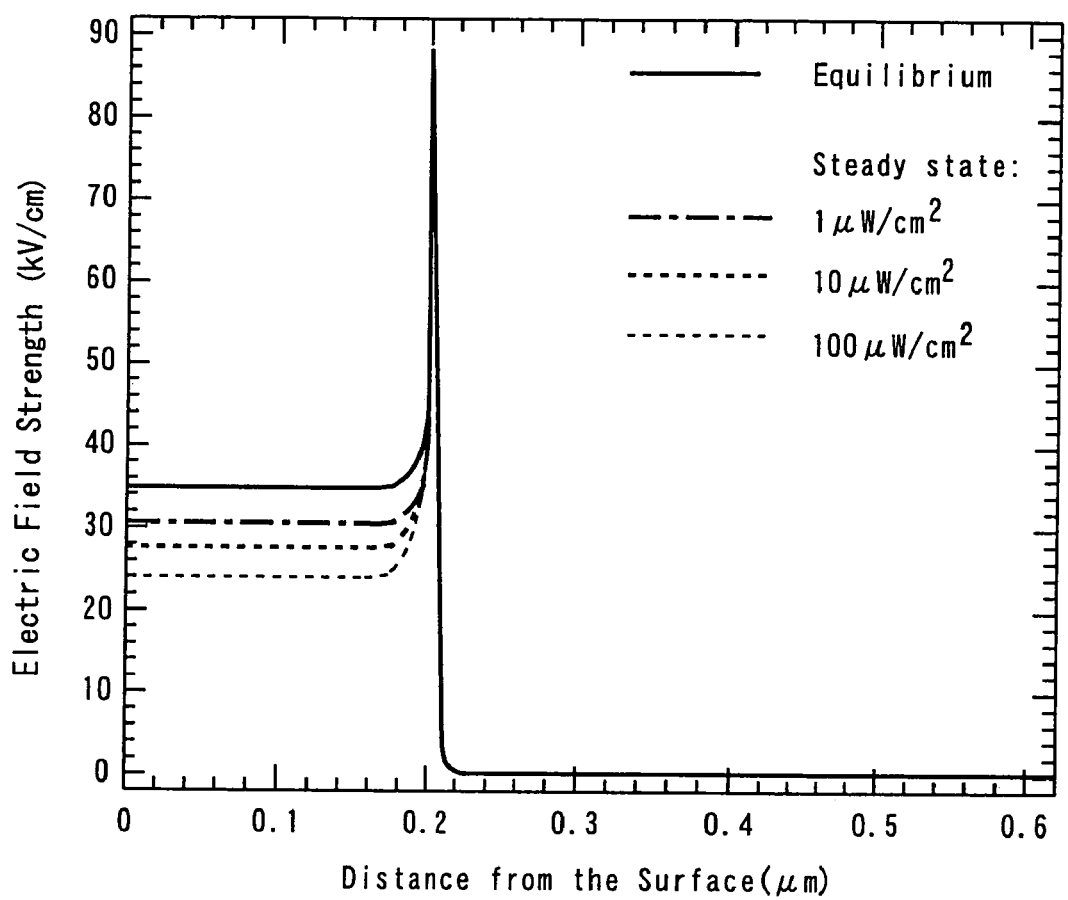
FIG. 7 shows built-in electric field strengths plotted as a function of distance from the sample surface.
Figure 8:
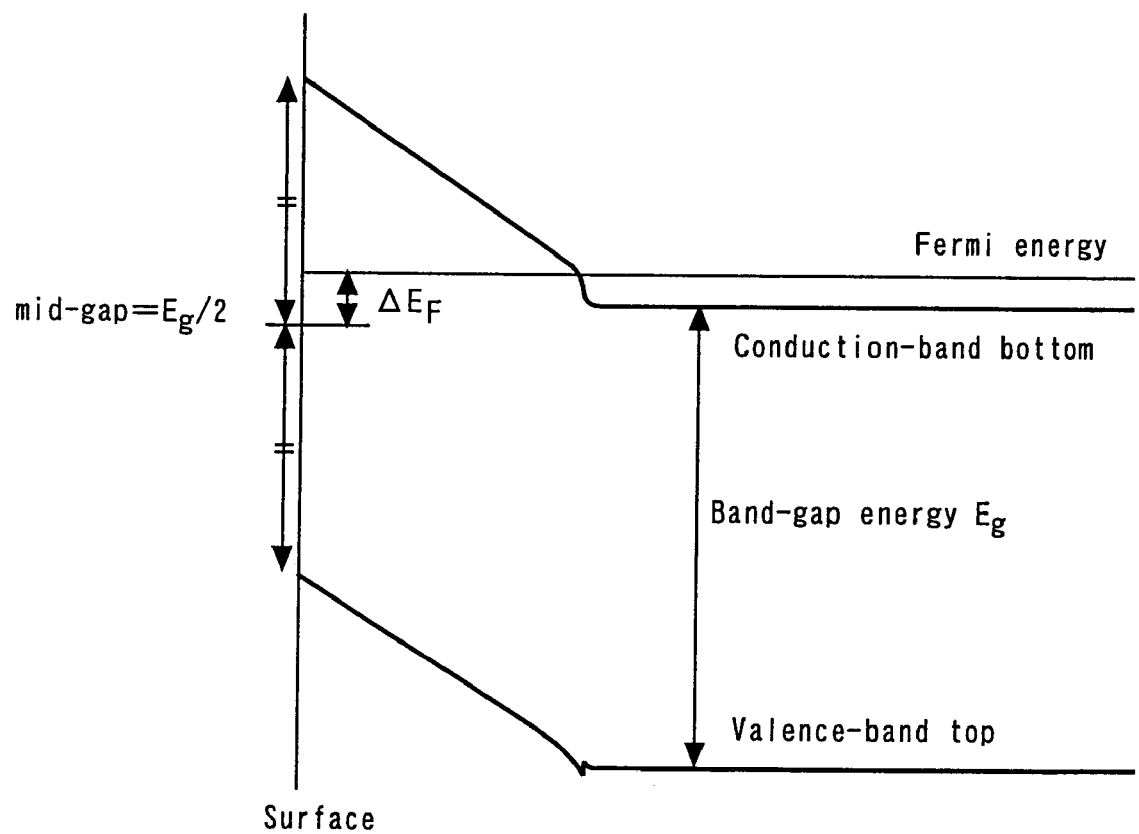
FIG. 8 shows an example of a potential diagram.

FIG. 7 shows the built-in electric field strengths in the i-GaAs/n-GaAs structure at various probe beam power densities plotted as a function of distance from the sample surface. The surface Fermi level and surface recombination velocity used for these calculations are ±0.0 eV and $2\times10^5$ cm/s, respectively. The value of the surface Fermi level is defined based on a mid-gap position as shown in FIG. 8. Therefore, the value of ±0.0 eV means that the surface Fermi level is pinned at the mid-gap, while the positive value (or negative value) denotes such a state that the surface Fermi level is located between a conduction band (valence band) and the mid-gap.

In FIG. 7, the solid line indicates the state at the absence of the probe-beam irradiation, so that it corresponds to a built-in electric field at equilibrium. The other lines indicate the states at the presence of the continuous irradiation of the probe beam, so that they correspond to steady-state built-in electric fields. The dashed-and-dottted line, the dashed line, and the dotted line correspond to built-in electric field strengths at the probe beam power densities of 1.0, 10, and 100 μW/cm$^2$, respectively. The peak appearing at the distance of 0.2 μm from the surface results from a band-gap energy difference between the n-GaAs layer and the i-GaAs layer, which is caused mainly by a band-gap shrinkage in the n-GaAs layer. The built-in electric field is distributed uniformly in the i-GaAs layer except for the peak. The point noteworthy here is that the surface electric field strength is reduced by irradiation of the probe beam with μW/cm$^2$-order power density. This denotes that the built-in electric field strength is sensitive to the probe beam power density. This phenomenon is a consequence of photovoltaic effect on the surface electric field.

In order to examine the relations among the photovoltaic effect, the surface Fermi level, and the surface recombination velocity, the present inventors calculated surface electric field strengths at various probe beam power densities using various sets of the surface Fermi level and the surface recombination velocity. The calculated surface electric field strengths are plotted as a function of probe beam power density in FIGS. 9A and 9B.

Figure 9B:
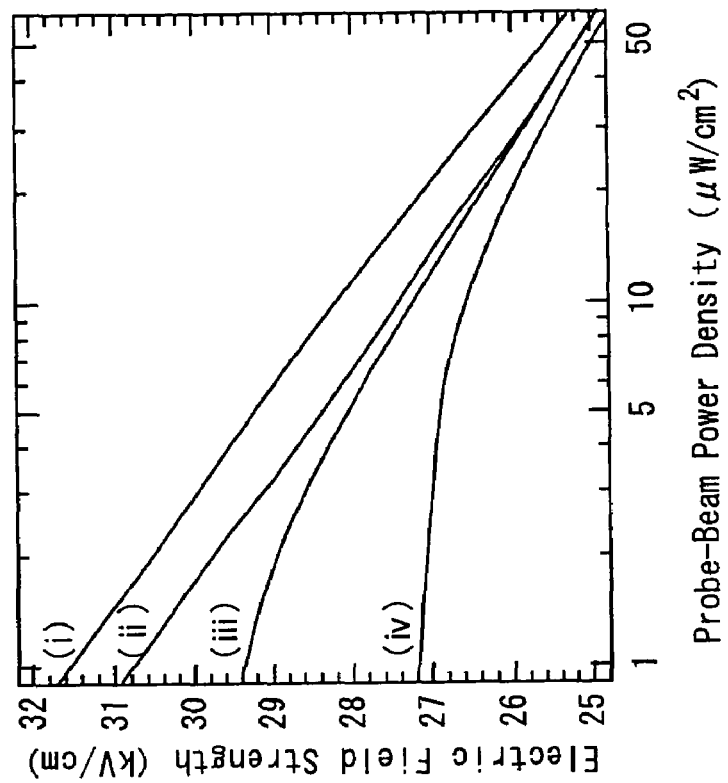
FIG. 9B shows surface electric field strengths as a function of probe beam power density calculated at various surface Fermi levels.
Figure 9A:
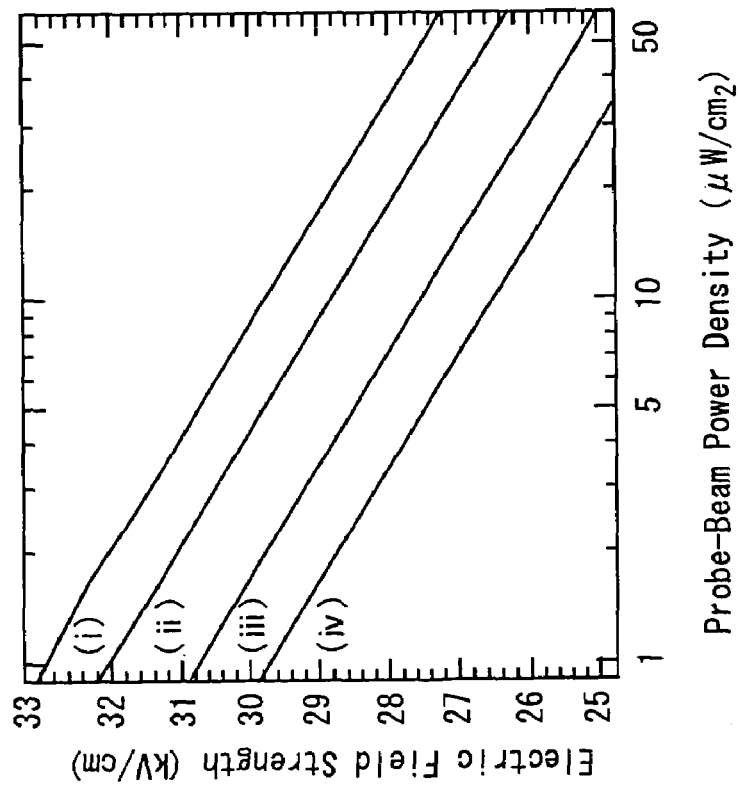
FIG. 9A shows surface electric field strengths as a function of probe beam power density calculated at a various surface recombination velocities.

FIG. 9A shows resulting curves plotted with a fixed surface Fermi level of ±0.0 eV while varying the surface recombination velocity, where the curve (i) is plotted at a surface recombination velocity of $1.0\times10^6$ cm/s, the curve (ii) is plotted at $5.0\times10^5$ cm/s, the curve (iii) is plotted at $2.0\times10^5$ cm/s, and the curve (iv) is plotted at $1.0\times10^5$ cm/s.

FIG. 9B shows resulting curves plotted at a fixed surface recombination velocity of $2.0\times10^5$ cm/s while varying the surface Fermi level, where the curve (i) is plotted with a surface Fermi level of −0.10 eV, the curve (ii) is plotted with ±0.00 eV, the curve (iii) is plotted with +0.10 eV, and the curve (iv) is plotted with +0.15 eV.

The calculations of surface electric field strengths shown in FIG. 9A are performed by varying the surface recombination velocity from $1.0\times10^5$ cm/s for (iv) to $1.0\times10^6$ cm/s for (i) while fixing the surface Fermi level to ±0.0 eV. In contrast, the calculations of surface electric field strengths shown in FIG. 9B are performed by varying the surface Fermi level from −0.10 eV for (i) to +0.15 eV for (iv) while fixing the surface recombination velocity to $2.0\times10^5$ cm/s.

As shown in FIG. 9A, the surface electric field strength is enhanced as the surface recombination velocity increases. It is considered that the enhancement of the surface electric field strength is caused by the suppression of the photovoltaic effect due to the decrease in carrier density. This is because an increase in surface recombination velocity makes the effective carrier lifetime short, and hence reduces the steady-state carrier density. The present inventors also calculated electron densities at the surfaces for different surface recombination velocities in order to examine the relation between the carrier density and the surface recombination velocity.

It is obtained from the calculations that the surface electron densities at surface recombination velocities of $1.0\times10^5$ and $5.0\times10^5$ cm/s are $1.2\times10^8$ and $2.3\times10^7$ cm$^{-3}$, respectively. These calculations are performed at the probe beam power density of 5.0 μW/cm$^2$ and the surface Fermi level of ±0.0 eV. The calculation results support that the carrier density strongly depends on the surface recombination velocity.

The following descriptions indicate the shapes of curves shown in FIGS. 9A and 9B obtained by plotting the surface electric field strengths as a function of probe beam power density. The shapes of respective curves shown in FIG. 9A reveal that the surface electric field strengths have a linear dependence on the logarithm of the probe beam power density. In contrast, the shapes of curves shown in FIG. 9B exhibit saturation characteristics in low probe beam power density range as the surface Fermi level approaches to the bottom of the conduction band. Therefore, it is concluded that the shapes of the curves are sensitive to a combination of the two parameters, the surface Fermi level and the surface recombination velocity. This conclusion means that both the surface Fermi level and the surface recombination velocity can be determined from the dependence of the surface electric field strength on the probe beam power density.

It is important to make clear the mechanism producing differences in curve shape in order to make it certain that this analysis is physically meaningful, that is, to verify the effectiveness and appropriateness of the analysis method.

The differences in curve shape can be explained based on the theory on the open-circuit photovoltage of solar cells. According to the theory, steady-state surface potential barrier $V_B$ corresponding to an energy difference between the Fermi level and the bottom of the conduction band during irradiation of the probe beam is expressed as follows:

[Eq. 7]

$$V_B = V_{B,0} - \frac{\gamma k_B T}{e} \ln\left\{\frac{J_{PC}}{J_0(T)} + 1\right\} \quad (7)$$

In this equation, $V_{B,0}$ denotes a potential barrier height at equilibrium, $k_B$ is the Boltzmann constant, e is the elementary charge, T is temperature, and $\gamma$ is an ideal factor. The physical quantities $J_{PC}$ and $J_O$ are the photo-induced current (photocurrent) and saturation current (dark current), respectively. In Equation (7), the second term corresponds to the photovoltaic effect.

The saturation current density in the second term mainly consists of thermal emission and diffusion at room temperature, while the photo-induced current density is in proportion to the probe beam power density. Based on the approximation that neglects corrections for the Debye length and space charge, the steady-state potential barrier is given by:

$$V_B \approx F_s d_{i\text{-}GaAs} \quad (8)$$

where $F_s$ and $d_{i\text{-}GaAs}$ denote the surface electric field strength and the thickness of the i-GaAs layer in the steady state, respectively. Equation (8) can be modified as follows:

[Eq. 9]

$$F_s \approx F_{s,0} - \frac{\gamma k_B T}{e d_{i\text{-}GaAs}} \ln\left\{\frac{J_{PC}}{J_0(T)} + 1\right\} \quad (9)$$

where $F_{s,0}$ is the surface electric field strength at equilibrium.

It is apparent from this equation that the steady-state surface electric field strength is in proportion to the logarithm of the probe beam power density in one criterion of $J_0 \ll J_{PC}$. In contrast, the steady-state surface electric field strength in the other criterion, that is, $J_0 \gg J_{PC}$, is saturated in low probe beam power density range. It is, therefore, considered that the linear dependence shown in FIG. 9A results from the former criterion, while the saturation characteristics in FIG. 9B result from the latter criterion.

Figure 10A:
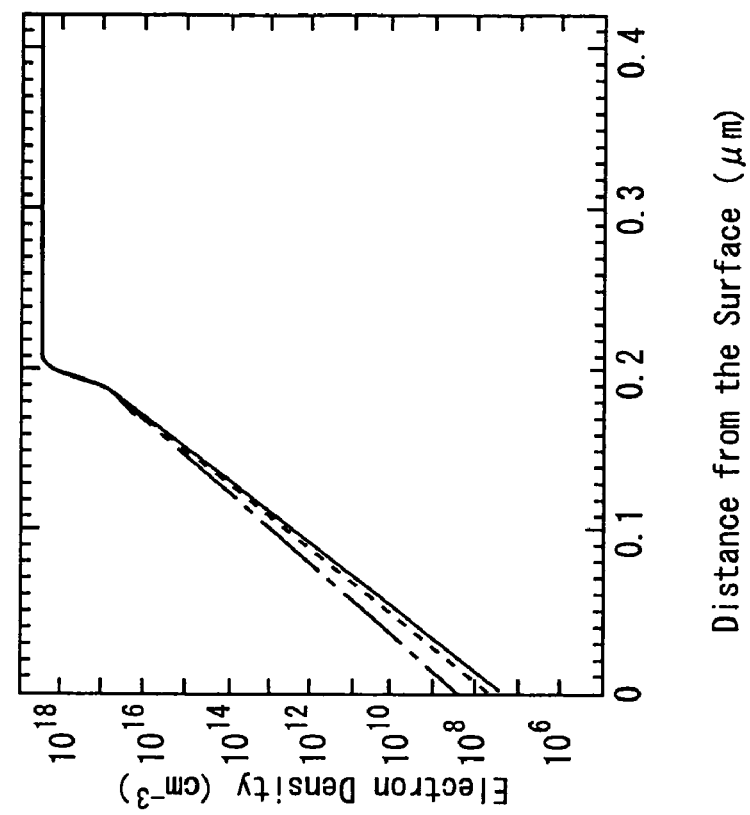
FIG. 10A shows distributions of electron density as a function of distance from the surface at the surface recombination velocity of $2.0 \times 10^5$ cm/s and the surface Fermi level of ±0.0 eV.
Figure 10B:
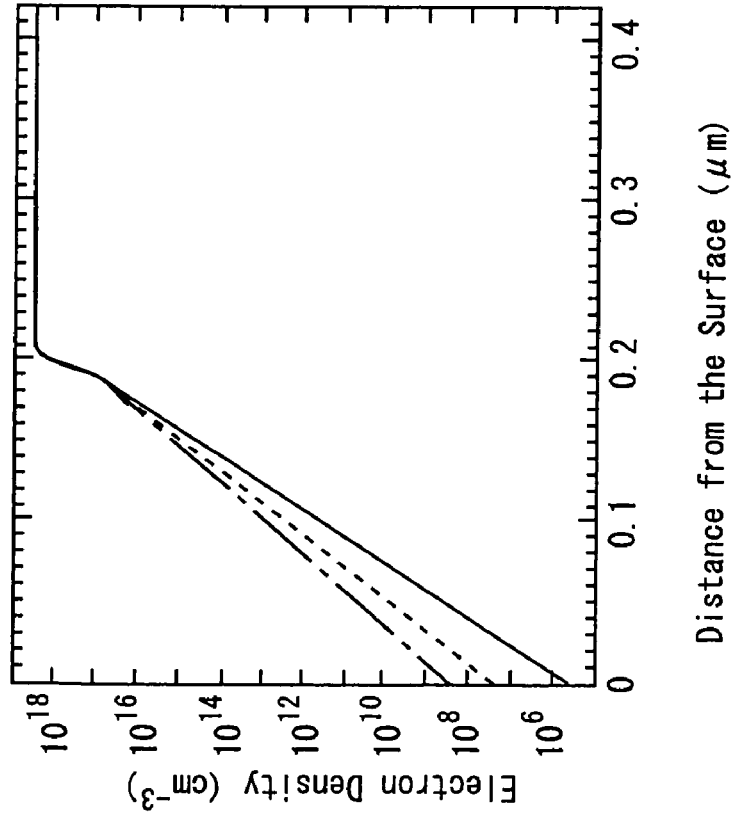
FIG. 10B shows distributions of electron density as a function of distance from the surface at the surface recombination velocity of $2.0 \times 10^5$ cm/s and the surface Fermi level of ±0.10 eV.

The present inventors examined distributions of carrier density in order to confirm the above-mentioned consideration. FIGS. 10A and 10B show distributions of electron density as a function of distance from the surface. In calculating the distributions of electron density as shown in FIGS. 10A and 10B, the same value of $2.0 \times 10^5$ cm/s is adopted for the surface recombination velocity.

On the other hand, different values of ±0.0 eV and +0.10 eV are adopted for the surface Fermi level. This means that the distributions of electron density shown in FIGS. 10A and 10B are calculated using the same parameters as those for the curve (iii) in FIG. 9A and those of the curve (iii) in FIG. 9B, respectively.

The solid lines in FIGS. 10A and 10B exhibit electron density distributions at equilibrium. On the other hand, the other lines exhibit steady-state electron density distributions. The probe beam power densities used in calculating the dashed curve and the dashed-and-dotted curve are 2.0 and 20 μW/cm², respectively. It is apparent that the equilibrium electron density distributions in the i-GaAs layer is sensitive to the surface Fermi level. The surface electron density shown in FIG. 10B is about 50 times higher than that in FIG. 10A. Based on Boltzmann statistics, equilibrium surface electron density $n_s$ is represented by the following equation:

[Eq. 10]

$$n_s = n_{n\text{-}GaAs} \exp\left(-\frac{V_{B,0}}{k_B T}\right) \quad (10)$$

There is a difference of 0.1 eV between two values for the equilibrium potential barrier height corresponding to the surface Fermi level used for the calculations. According to Equation (10), the equilibrium surface electron density shown in FIG. 10B exhibits about $\exp(0.1/k_B T) \approx 50$ higher than that in FIG. 10A at room temperature ($k_B T$=26.0 meV). From this point of view, it is considered that a difference in surface Fermi level originates from the difference in electron density.

As shown in Equation (7) and Equation (9), the photovoltaic effect is suppressed as the steady-state electron density approaches to the equilibrium electron density. FIG. 10B shows that the irradiation of probe beam with a power density of 2.0 μW/cm² only slightly increases the electron density. According to this fact, the curve (iii) in FIG. 9B deviates from the linear dependence in probe beam power beam density range of 5 μW/cm² or less and starts being saturated. This is a phenomenon attributed to the above-mentioned situation.

In contrast, when the steady-state electron density is sufficiently higher than the equilibrium electron density, corresponding portions of the curves shown in FIGS. 9A and 9B exhibit a linear dependence. From these results, it has been confirmed that the dependence of the electron density on the surface Fermi level is attributed to the parameters that determine the linear dependence of the surface electric field strength on the logarithm of the probe beam power density.

In calculating the surface electric field strength, various parameters are used as shown in Tables 1 and 2. Among these parameters, the bulk carrier lifetime and the mobility are sensitive to the crystallinity of a sample used. Such parameters vary from sample to sample. The uncertainty of bulk carrier lifetime and mobility seems to affect the fitting. However, the following calculation results show that the surface electric field strength is hardly affected by these two parameters. It means that the surface recombination velocity and the surface Fermi level can be determined precisely without influence of the uncertainty of bulk carrier lifetime and mobility.

Figure 11:
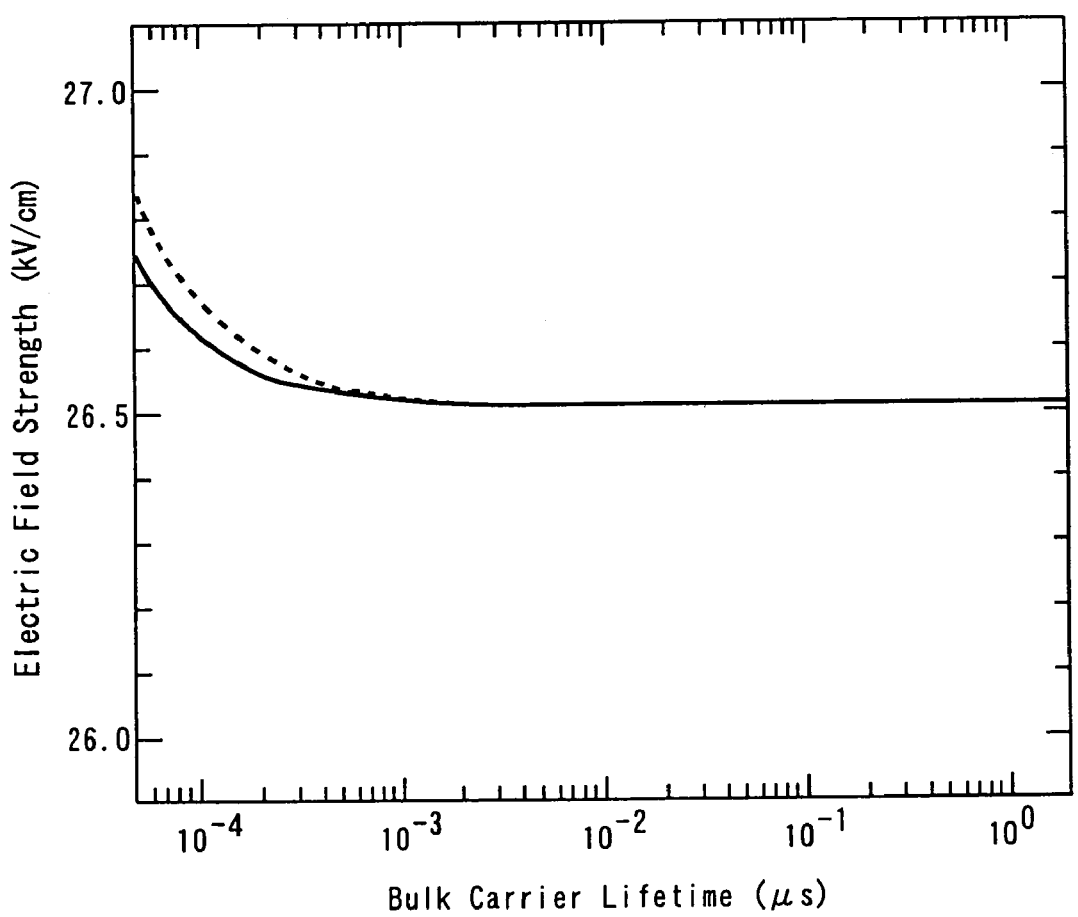
FIG. 11 shows surface electric field strengths as a function of bulk carrier lifetime.

FIG. 11 shows surface electric field strengths in the i-GaAs layer as a function of bulk carrier lifetime. The parameters used for the calculations are surface Fermi level of ±0.0 eV, surface recombination velocity of $2.0 \times 10^5$ cm/s, and probe beam power density of 20 µW/cm$^2$.

For the sake of simplification, the calculations are performed under the assumption that the electron and hole have the same bulk carrier lifetime.

The solid line in FIG. 11 is calculated using the same value of carrier mobility shown in Table 2. As shown in FIG. 11, even if the bulk carrier lifetime is changed from 1.0 to $5.0 \times 10^{-4}$ µs, a change in surface electric field strength is only 0.2 kV/cm. Since this value is 1.1 percent of the surface electric field strength at most, it is considered that the influence of changes in bulk carrier lifetime is so small that it can be neglected.

This result can be qualitatively explained by the effective carrier lifetime in the i-GaAs layer. The effective carrier lifetime, $\tau_{eff}$, is represented by the following equation:

[Eq. 11]

$$\frac{1}{\tau_{eff}} = \frac{1}{\tau_{Bulk}} + \frac{S}{d_{i-GaAs}} \quad (11)$$

where $\tau_{Bulk}$ and S represent the bulk carrier lifetime and the surface recombination velocity, respectively.

The second term in this equation represents the effect of the surface recombination velocity. The value in the second term in the model sample structure used in the above-mentioned experiments can be estimated at 10 ns$^{-1}$ at a surface recombination velocity of $2 \times 10^5$ cm/s. This value is much larger than a reciprocal number (about 50 ns) of bulk carrier lifetime for a normal GaAs crystal. Therefore, it is concluded that the effective carrier lifetime from which the carrier density in the i-GaAs layer can be determined is mainly determined by the surface recombination. As shown in FIG. 11, the reciprocal number (=0.1 ns) of the second term substantially corresponds to a threshold at which the surface electric field strength shows a sharp increase with a decrease in the bulk carrier lifetime. This supports the above description based on the concept of the effective carrier lifetime.

The following descriptions indicate the influence of carrier mobility in the i-GaAs layer. The dashed line in FIG. 11 is obtained as a result of calculation using values of 2000 cm$^2$/Vs and 100 cm$^2$/Vs for electron and hole mobilities in the i-GaAs layer, respectively. It is apparent from FIG. 11 that the surface electric field strength is also hardly affected by changes in carrier mobility. This result can be explained by the relation between photo-induced current density and carrier mobility as shown in the following equation:

[Eq. 12]

$$J_{PC} = J_{PC,\infty}\left(1 - \frac{d_{i-GaAs}^2}{\mu\tau V_{B,0}}\right) \quad (12)$$

where $J_{PC,\infty}$ is the photo-induced current density when the carrier mobility is set to be equal to infinity. The quantity µτ is a physical quantity, called an average mobility-carrier lifetime product, which is expressed as

[Eq. 13]

$$\mu\tau = \frac{2\mu_e\tau_e\mu_h\tau_h}{\mu_e\tau_e + \mu_h\tau_h} \quad (13)$$

where $\mu_{e(h)}$ and $\tau_{e(h)}$ are electron (hole) mobility and bulk carrier lifetime in the i-GaAs layer, respectively.

Equation (12) shows that bulk recombination causes a loss in photo-induced current density originating from a finite carrier mobility. Apparently, if the value in the second term is so small that it can be neglected, the influence of the carrier mobility can be neglected. In order to examine the influence of the second term, the present inventors calculated the denominator in the second term using the following parameters: the electron mobility of 2000 cm$^2$/Vs, hole mobility of 100 cm$^2$/Vs, bulk carrier lifetime of 1.0 ns, and equilibrium potential barrier height of $E_{g,0}/2e$ (=0.712 V).

The value of the denominator calculated using these parameters is $1.4 \times 10^{-7}$ cm$^2$, which is much larger than the value of the numerator the square of the i-GaAs layer thickness ($4 \times 10^{-10}$ cm$^2$). Accordingly, it is considered that the photo-induced current density hardly depends on the carrier mobility. This means that the surface electric field strength is hardly affected by the carrier mobility. From the above-mentioned results, it is concluded that the analysis technique according to the present invention has the advantage of determining both the surface Fermi level and the surface recombination velocity precisely at the same time without influence of the other parameters.

When the surface Fermi level and the surface recombination velocity are determined by the above-mentioned analysis method, a spectroscopic apparatus for measuring data to be analyzed requires the following capabilities:

(1) It does not change the surface electric field strength during measurement.

(2) It can detect FK oscillations with high precision.

Figure 12:
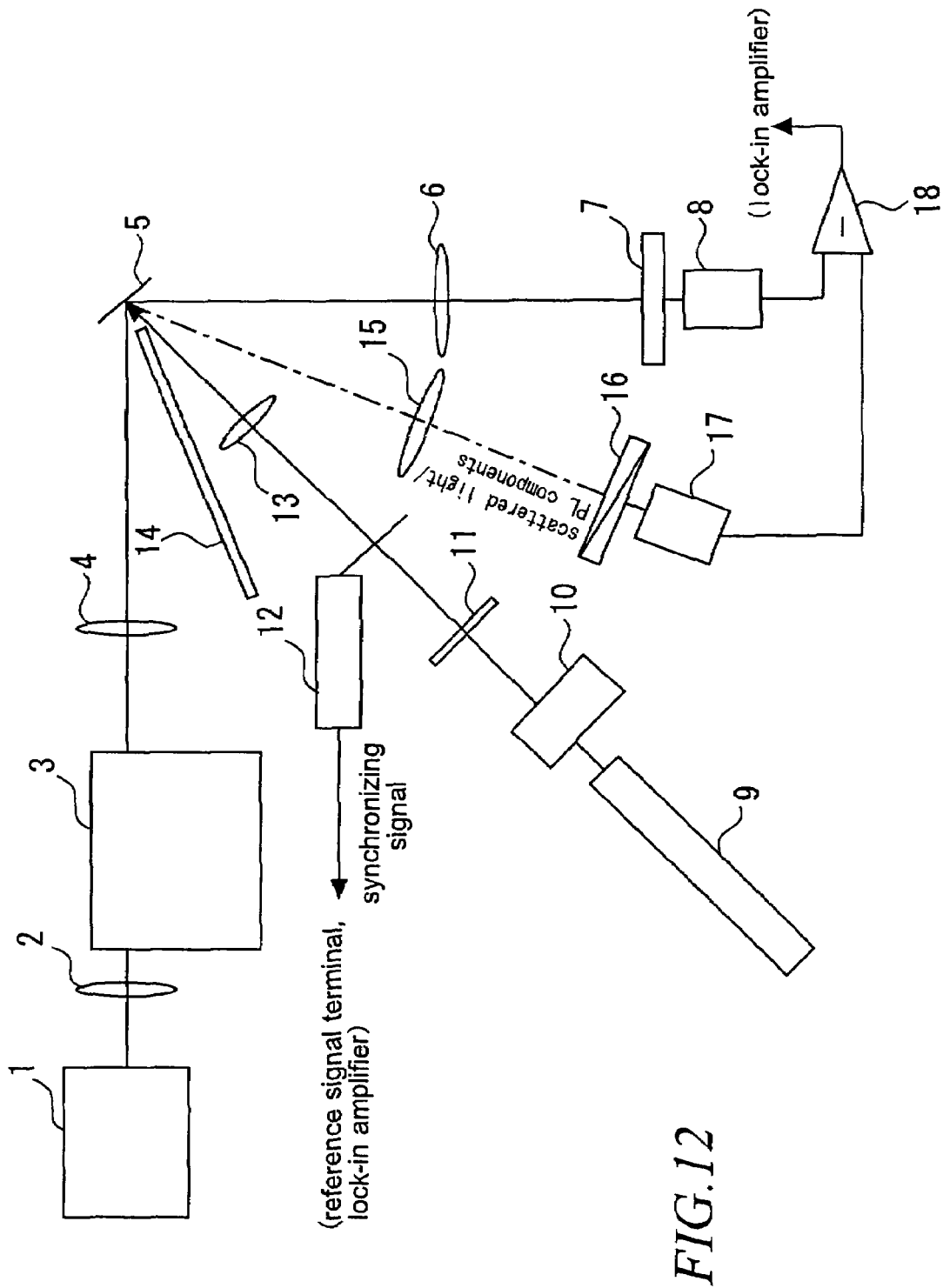
FIG. 12 shows a schematic diagram of a structure of a PR measurement apparatus according to the present embodiment.

FIG. 12 shows an example of such a spectrometry apparatus that meets the above-mentioned capability requirements. In FIG. 12, the same reference numerals are given to the same or corresponding parts as those in FIG. 5, and their explanation is omitted. The differentces from FIG. 5 are the following two mechanisms that are provided in FIG. 12:

Mechanism (1): A temperature control mechanism 14 (a gas inlet tube) for blowing a jet of gas onto the sample 5 to prevent change in the surface temperature of the sample 5 so that the surface electric field strength of the sample 5 can be maintained to be constant; and Mechanism (2): A signal detection system mainly composed of a differential circuit 18 for recording the signal due to FK oscillations with high precision without influence of the unwanted signal arising from disturbance light.

For these mechanisms, an attenuator 16 for balance correction is provided for condensing scattered light and PL components through a condenser lens 15, while a reference signal detector 17 is provided for generating reference signals for correcting the scattered light and the PL components based on the output of the attenuator 16. In this structure, the differential circuit 18 amplifies the difference component between the signal from the detector 17 and the signal from the PR signal detector 8.

The following descriptions indicate the details and advantages of the measurement apparatus according to the embodiment.

The details and advantages of the mechanism (1) are as follow: As discussed above, the surface electric field strength of the sample 5 is sensitive to the surface Fermi level and the surface recombination velocity, but hardly depends on the bulk carrier lifetime and mobility. Since the other parameters, for example, the band-gap energy and refractive index, are physical constants inherent in the sample, they have been examined in detail up to now. Therefore, the uncertainty of these parameters is almost negligible.

It can thus be considered that there is no influence of the parameters inherent in the sample on the extraction of the surface Fermi level and the surface recombination velocity from the surface electric field strength. However, the surface electric field strength is sensitive to parameters resulting from an environment outside of the sample, especially to temperature.

Figure 13:
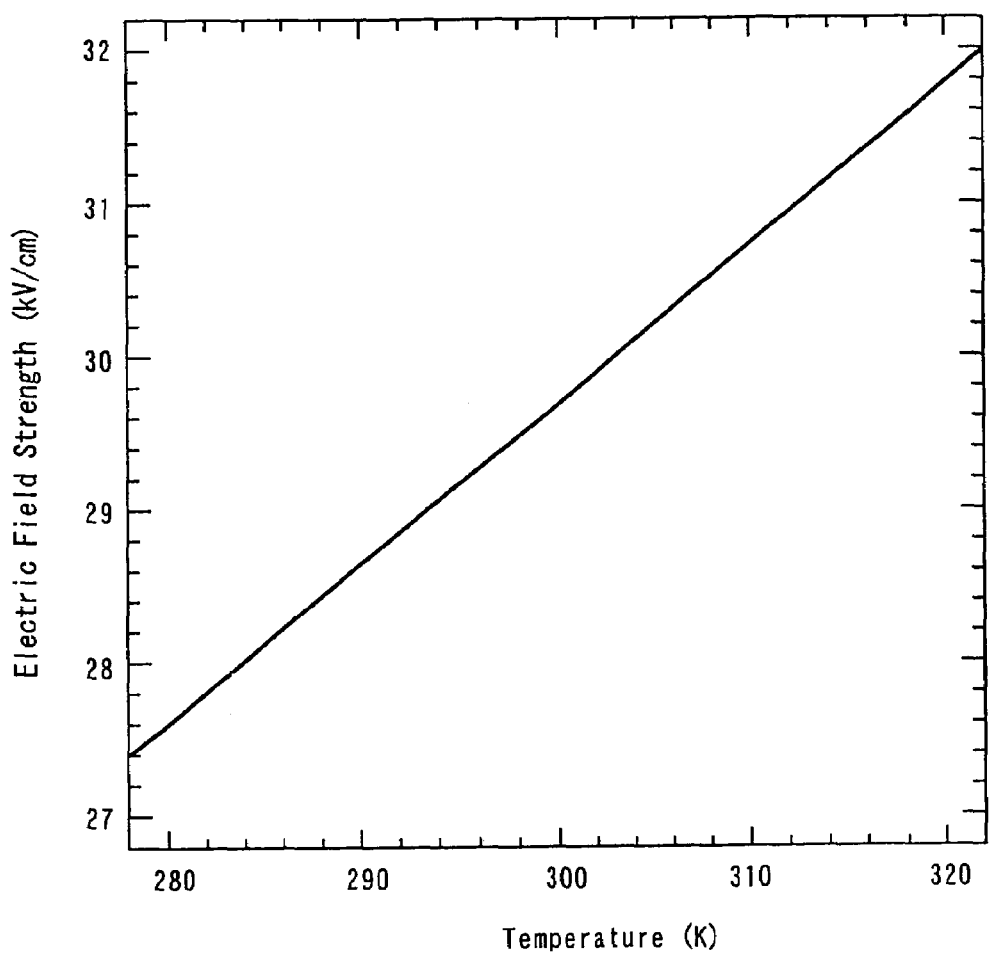
FIG. 13 shows a surface electric field strength plotted as a function of temperature.

FIG. 13 shows calculated surface electric field strength plotted as a function of temperature. The parameters used for the calculation are surface recombination velocity of $5 \times 10^5$ cm/s, surface Fermi level of ±0.0 eV, and probe beam power density of 5.0 µW/cm$^2$.

It is apparent from FIG. 13 that the surface electric field strength changes by about 1 kV/cm with just a slight temperature change by about ten degrees Celsius. Since the sample surface temperature rises as the pump beam is irradiated in the PR measurement, it is necessary to attach, to the measurement apparatus, a mechanism for preventing a temperature rise of the sample surface in order to determine the surface electric field strength precisely from PR spectra.

Figure 14:
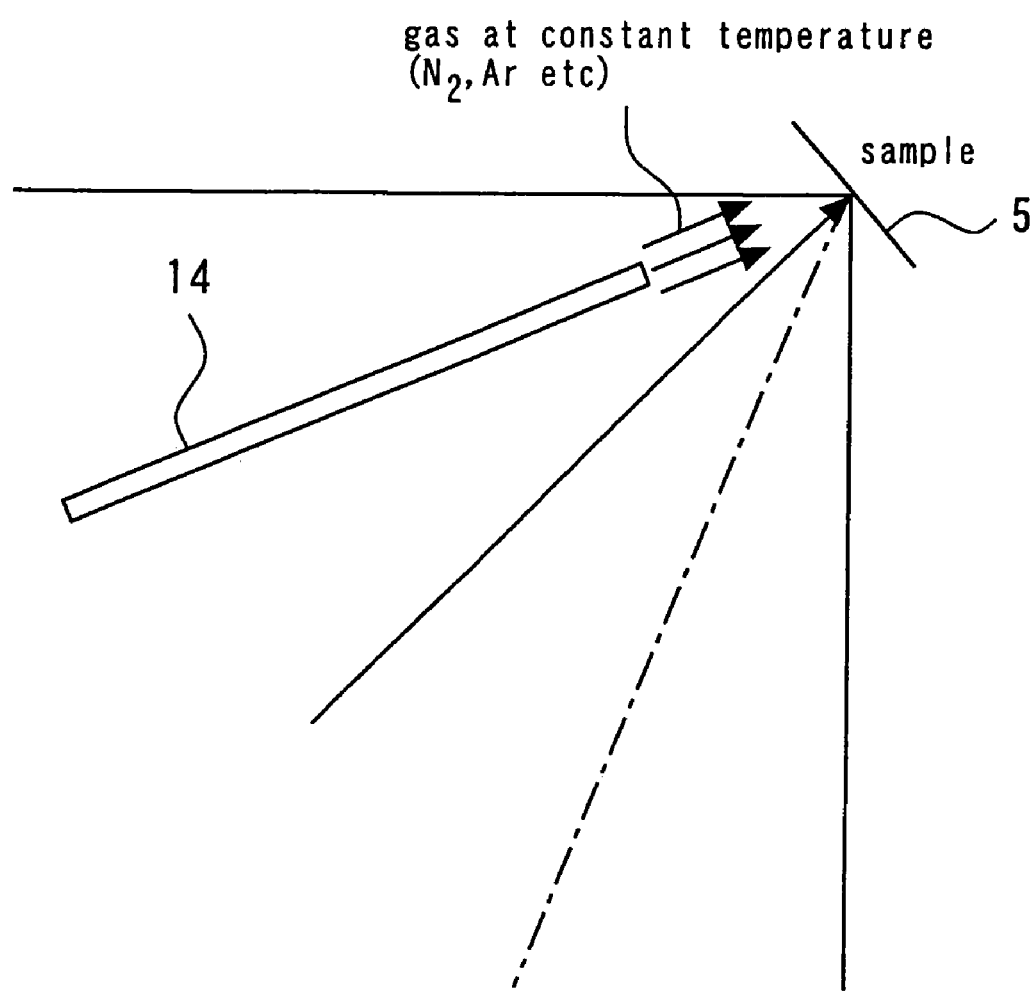
FIG. 14 is an enlarged view of the mechanism for preventing a surface temperature rise of the sample in the measurement apparatus shown in FIG. 12.

FIG. 14 is an enlarged view of the mechanism for preventing a surface temperature rise of the sample 5 in the measurement apparatus shown in FIG. 12. This mechanism can blow a jet of gas at constant temperature onto an area irradiated with the pump beam. Since the pump beam and the probe beam used in the PR measurement are not so strong, they raise the temperature by just about 10 degrees Celsius. Therefore, the relatively simple mechanism shown in FIG. 14 is enough to prevent the temperature rise of the sample surface and hence to enable the precise measurement of the surface electric field strength at a low cost.

The gas to be blown is dry inert gas, such as rare gasses, nitrogen gas, or a mixture of these gasses, which can prevent the absorption of oxygen or moisture into the sample surface, and hence remove uncertainties, that is, changes in surface electric field strength, due to the absorption of oxygen or moisture.

The details and advantages of the mechanism (2) are as follow: There is the case where measurements are made by increasing the number of probe beam power density conditions in order to measure the surface Fermi level and the surface recombination velocity more precisely.

In this case, the measurements must be made under low probe beam power density conditions. In the normal PR measurement conditions, the detector 8 for detecting the probe beam reflected from the sample 5 captures not only the probe beam component to be measured, but also, as disturbance light, a mixture of pump beam components scattered on the sample surface and PL components generated by pump beam irradiation.

When a signal is sent from the detector 8 to the measurement unit such as the lock-in amplifier for detecting a modulated, reflected component, the disturbance light originating from the pump beam is recorded together with the modulated, reflectance component because the disturbance light is in phase with the modulated reflectance component of the probe beam from the sample. The pump beam used in the actual measurement contains a pattern of fluctuations and noise varying with time. Under low probe beam power density conditions, such noise components may interfere to detect the modulated reflection component in the probe beam. In addition, since the lock-in amplifier has the upper limit of its range, if amplifying the modulated reflection component and the disturbance light components at the same time, the sum of these components may reach the upper limit of the range even by amplifying a small amount of disturbance light, which results in inefficient amplification of the modulated reflectance component.

Figure 15:
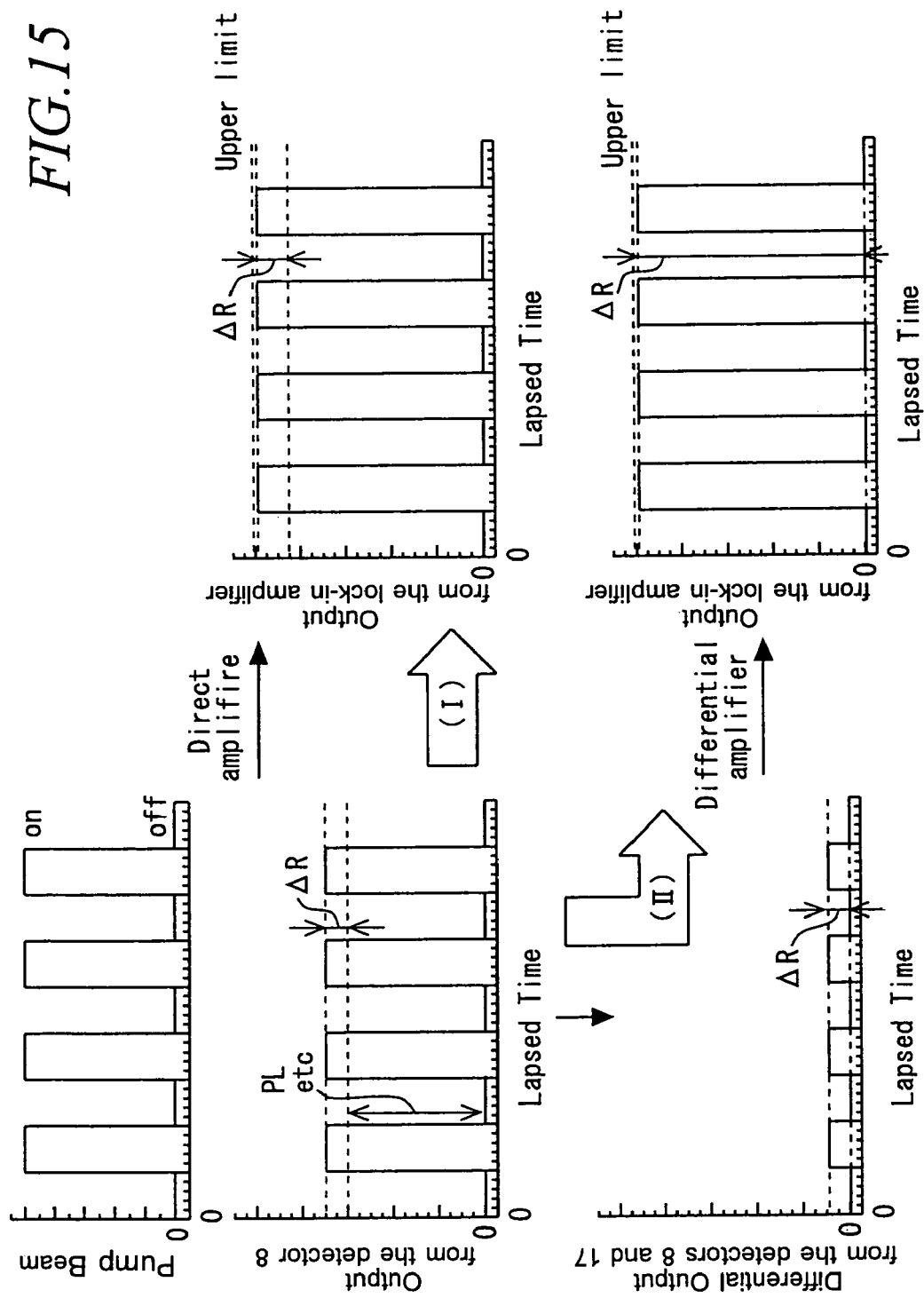
FIG. 15 is a diagram to explain a flow of detected signals and signal processing in the present embodiment.

A flow of signals schematically indicated by arrow (I) in FIG. 15 illustrates this problem. This corresponds to a direct way of supplying output of the detector 8 to the lock-in amplifier. Such a flow of signals makes it difficult to measure PR spectra precisely. It is, therefore, necessary to remove signals of disturbance light originating from the pump beam.

Among the signals to be removed, the pump beam components are relatively easy to remove. For example, the pump beam components can be inhibited from coming into the detector 8 both by using a pumping source having energy higher than that in photon energy range in which the FK oscillations are observed in the sample to be measured, and by providing an optical filter 7, such as a band-pass filter or short-cut filter, in front of the detector 8 to cut off the pump beam while transmitting light in the photon energy range in which the FK oscillations are observed.

However, it is impossible for the spectral filter to remove the PL components resulting from irradiation of the pump beam because the photon energy range of the spectra of the PL components overlaps with the photon energy range in which the FK oscillations are observed. Thus, the removal of the PL components generated by irradiation of the pump beam has been one of important problems in the PR measurement.

Figure 16:
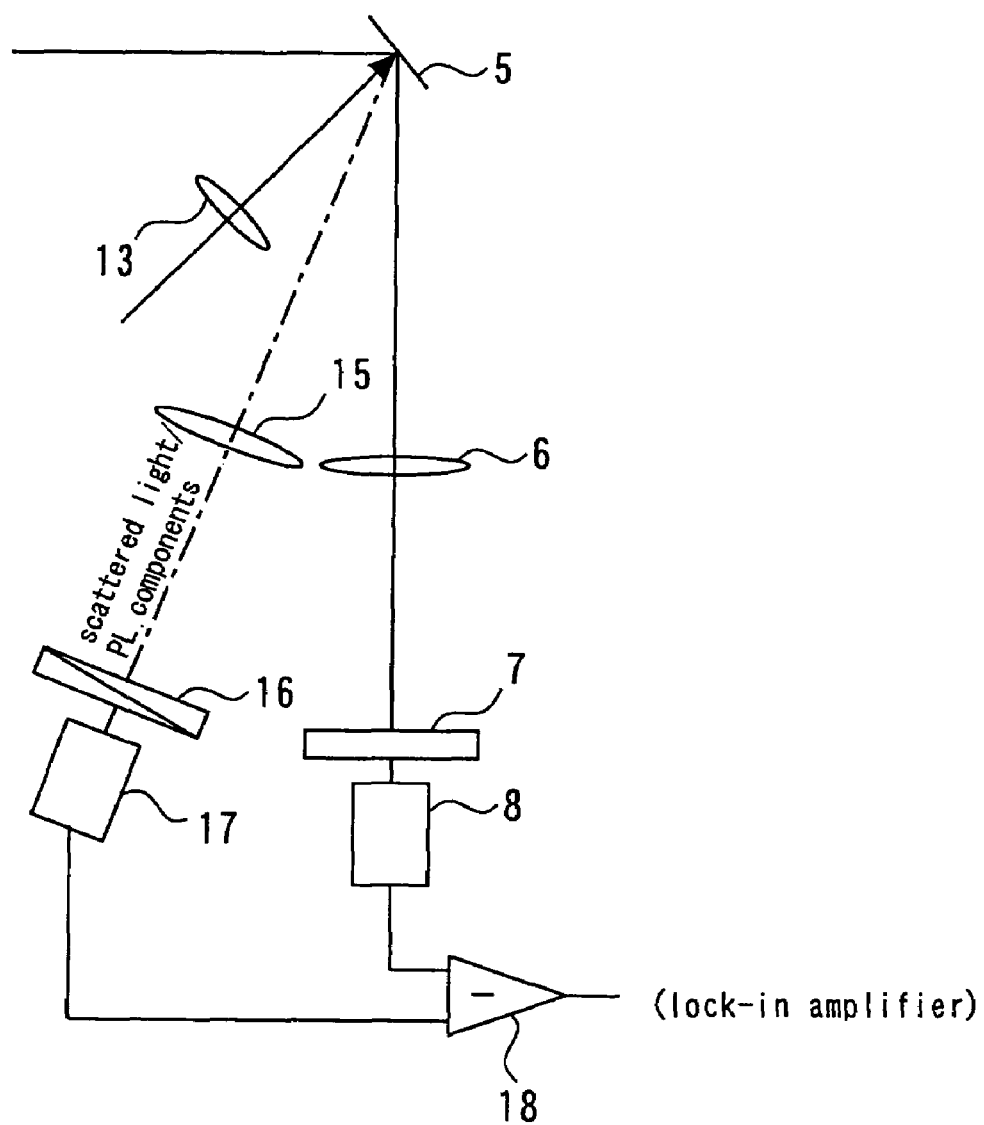
FIG. 16 is an enlarged view of the detection system comprising the differential circuit in FIG. 12.

The detection system mainly composed of the differential circuit 18 in FIG. 12 is the mechanism capable of removing the PL components. FIG. 16 is an enlarged view of this mechanism. In this system, the detector 17 for detecting the PL components and scattered light components from the sample is provided separately from the detector 8 used in the measurement system shown in FIG. 5. The difference signal between the signals obtained from the two detectors enables to subtract the PL components and the scattered light components, and thus only the modulated reflection signal detected by the detector 8 can be sent to the lock-in amplifier.

Since the signal sent to the lock-in amplifier does not contain any unnecessary signal component, the modulated reflection signal can be amplified and recorded efficiently. This corresponds to a flow of signals schematically indicated by arrow (II) in FIG. 15. Obtaining the difference signal leads to other advantages, such as to remove time-varying magnitude changes and noise components due to instability of the pump beam.

The above discussion is related to the method of observing the FK oscillations using the light modulation spectroscopy to extract the surface electric field strength. The FK oscillations can also be measured by any modulation spectroscopy other than the light modulation spectroscopy. Among others, contactless electroreflectance (hereinbelow abbreviated as CER) spectroscopy has the advantage of being able to measure the FK oscillations in a non-destructive and contactless manner. Therefore, the surface Fermi level and the surface recombination velocity may be extracted using the CER spectroscopy. The measurement and analysis procedures for extracting the surface recombination velocity and the surface Fermi level at the same time from the FK oscillations appearing in CER spectra are as follows:

(1) CER spectra are measured at various probe beam power densities using the CER spectroscopy.

(2) The period of the FK oscillations appearing in the CER spectra are analyzed to calculate surface electric field strengths.

(3) The surface electric field strengths obtained are plotted as a function of probe beam power density to perform analysis based on simulation fitting using various sets of the surface recombination velocity and the surface Fermi level.

Figure 17:
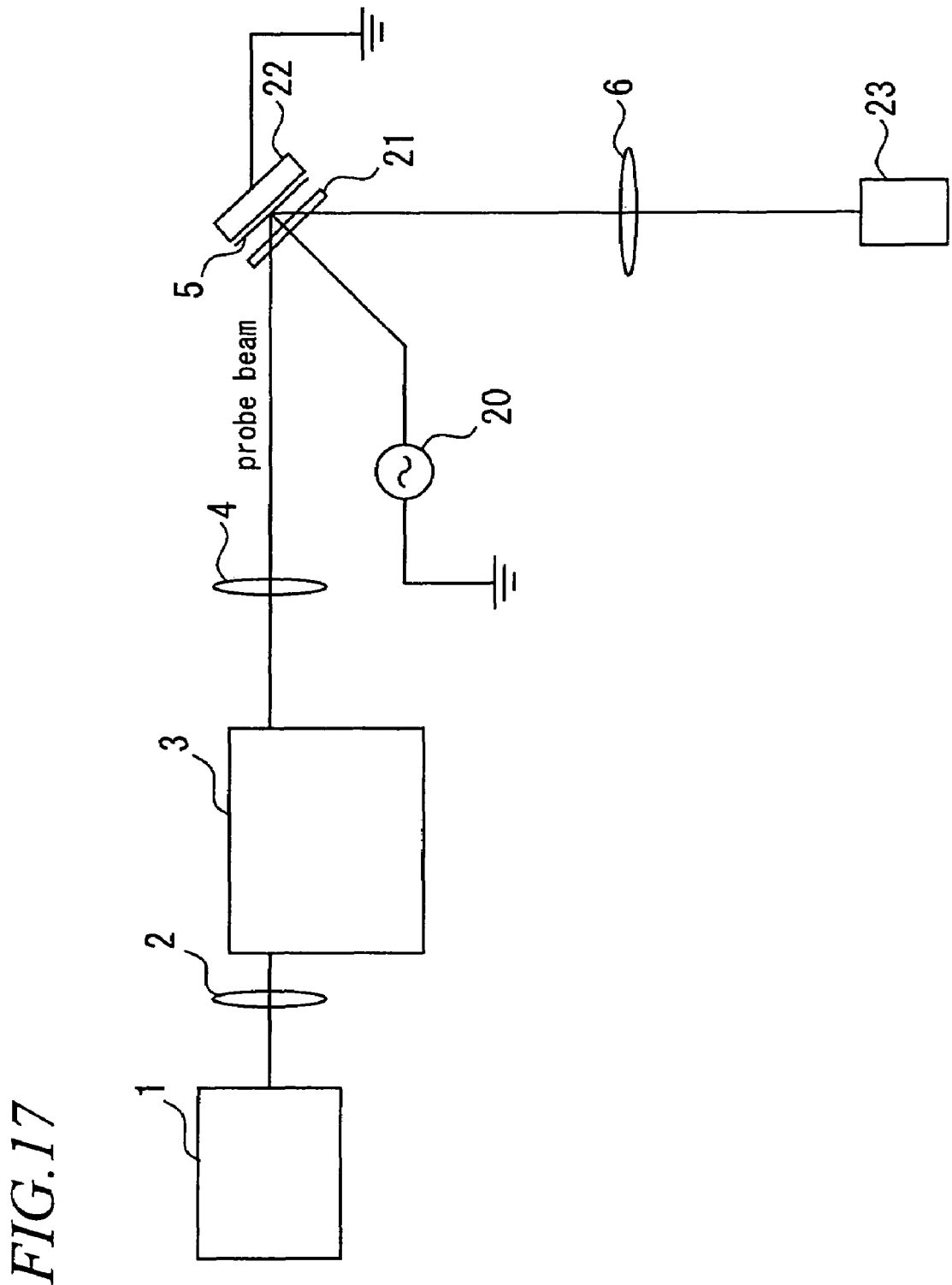
FIG. 17 is a schematic view of the structure of a CER measurement apparatus.

The following descriptions indicate the details of the measurement and analysis procedures. FIG. 17 is a schematic view of the structure of a CER measurement apparatus. The CER spectrum measurement using this apparatus is performed according to the following procedure:

(1) A periodically varying voltage is generated using an AC power supply 20 such as a pulse generator. The periodic voltage signal generated is branched in the way to the sample into one to be sent to a reference signal input terminal of the lock-in amplifier and the other to be sent to a voltage amplifier for generating voltage to be applied to the sample.

(2) The periodically varying voltage signal amplified by the voltage amplifier is applied between a transparent electrode 21 and a sample stage 22 on the back of the sample.

(3) The lock-in amplifier is adjusted to be in phase with the periodically varying voltage signal sent to the reference signal input terminal.

(4) Light from the white light source (e.g., lamp) 1 is guided to the monochrometer 3 for measuring a CER spectrum of the sample 5. The beam exiting from the monochrometer 3 in this state is a probe beam.

(5) The monochrometer 3 is swept across the spectrum so that a CER signal detector 23 will detect the probe beam.

(6) The detected signal is passed through the band pass filter to divide it into a DC component corresponding to reflectance R and an AC component corresponding to modulated reflectance ΔR.

(7) The DC component and the AC component are measured by the DC voltmeter and the lock-in amplifier, respectively.

(8) ΔR/R is calculated on a computer to obtain a CER signal.

(9) The steps (5) to (8) are repeated to record ΔR/R spectra as a function of wavelength λ or photon energy.

The analysis of data obtained in the measurements is performed in the same manner as that used in the PR measurement.

The following descriptions indicate the advantages of the measurement and analysis using the CER spectroscopy. As mentioned above, the CER spectroscopy does not need the pump beam. Therefore, it has the advantages of preventing a rise of the surface temperature caused by the pump beam, and disturbance light that has an adverse effect on the detection of the probe beam.

It also solves the problem in modulation spectroscopy that a level of photon energy (wavelength) of the pump beam must be selected as appropriate to the band-gap energy of the sample.

Figure 18:
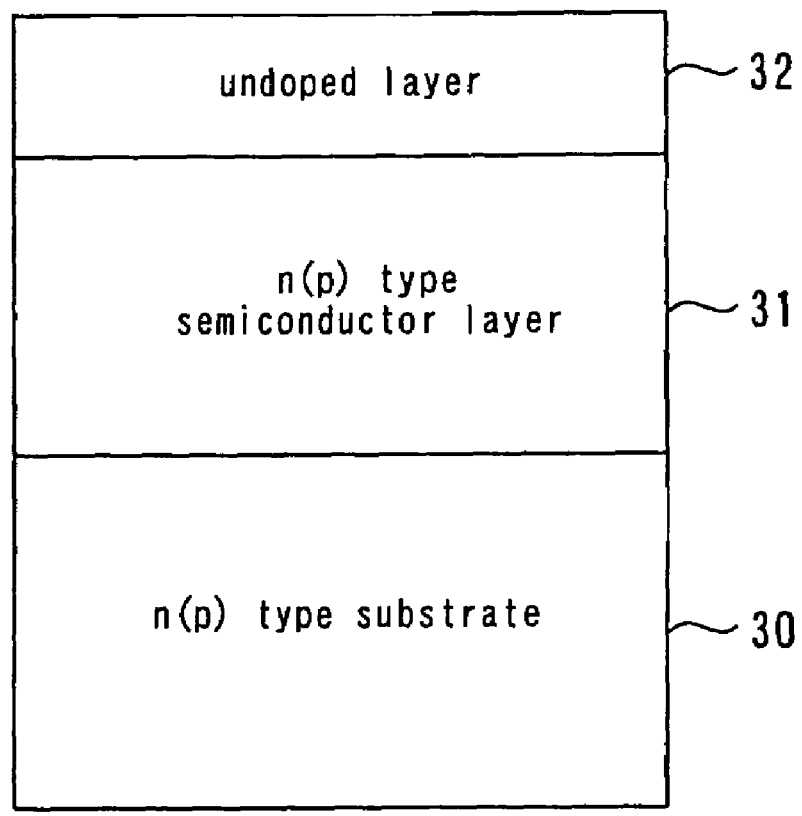
FIG. 18 shows a sample structure for high-precision measurement.

Apparently, the more the oscillation patterns observed upon analyzing the FK oscillations, the more precisely the electric field strength can be estimated. It is generally known that the number of oscillation patterns observed depends on the structure of the sample to be measured. A sample structure for high-precision measurement has been proposed which is a three-layer structure composed of, as shown in FIG. 18, an n- or p-type substrate 30, an n- or p-type semiconductor layer 31, and a high-resistivity or undoped layer 32.

The doping concentration and mobility obtained by measuring the sample, of course, can be used for the simulation to determine the surface recombination velocity and the surface Fermi level more precisely. In the above sample structure, however, it is impossible to determine the doping concentration and mobility of the semiconductor layer 31 in a non-destructive and contactless manner because the measurement of them are affected by the doped substrate.

Figure 19B:
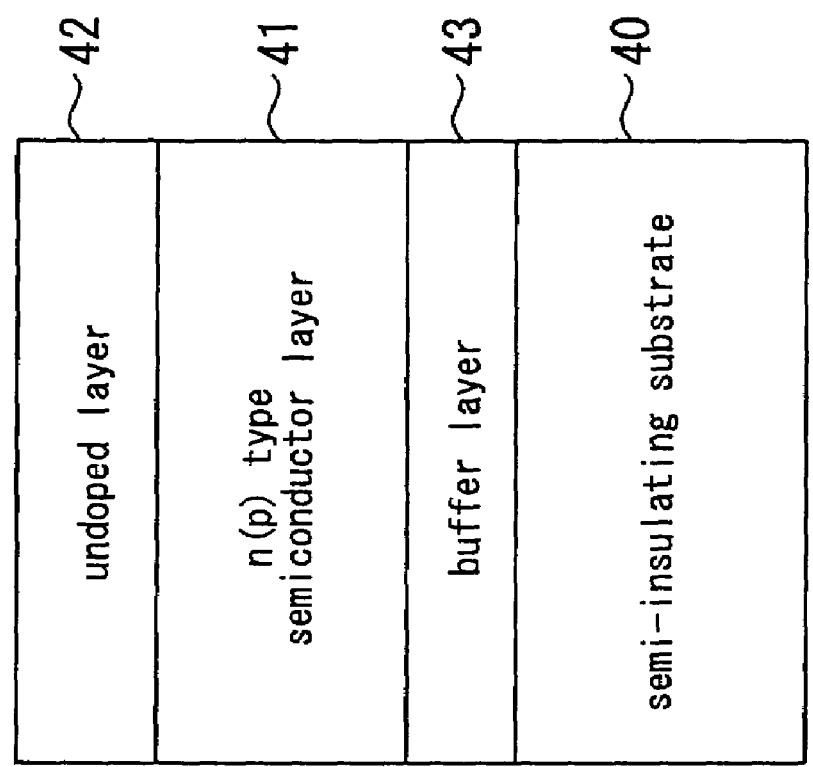
FIG. 19B shows other sample structure having a buffer layer for high-precision measurement of FK oscillations.
Figure 19A:
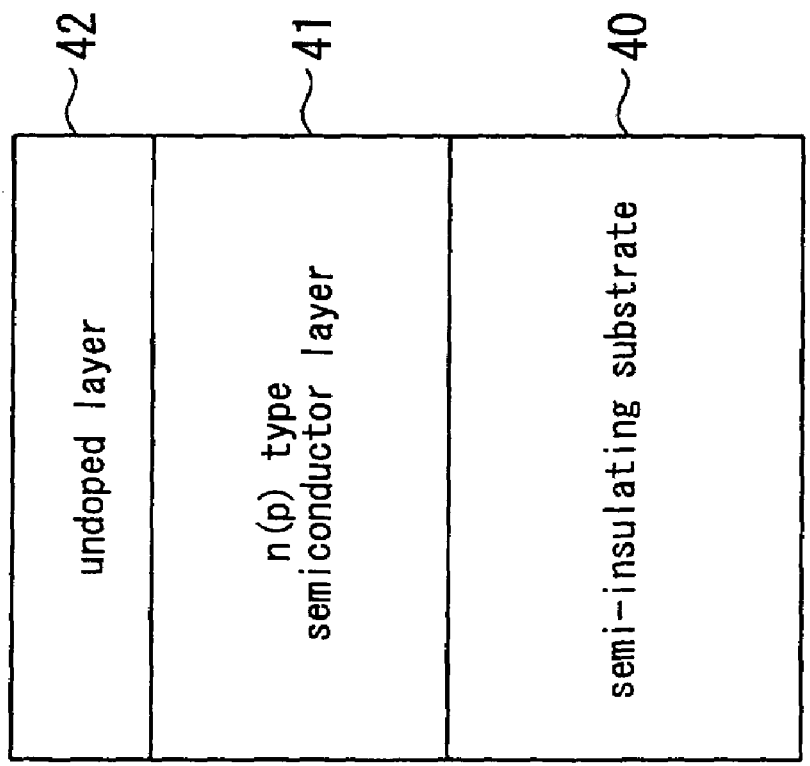
FIG. 19A shows other sample structure having no buffer layer for high-precision measurement of FK oscillations.

Solving this problem is a sample structure for high-precision measurement of FK oscillations, which is composed of a high-resistivity (semi-insulating) substrate 40, an n- or p-type semiconductor layer 41, and a high-resistivity or undoped layer 42. This structure is shown in FIG. 19A. Note that such a sample structure, as shown in FIG. 19B, with a buffer layer 43 inserted into the interface between the high-resistivity (semi-insulating) substrate 40 and the n- or p-type semiconductor layer 41 can also be used to solve the above problem. These structures, however, generate a built-in electric field between the substrate 40 and the upper layer 41.

Therefore, it is necessary to prevent FK oscillations caused by the built-in electric field from appearing in the spectrum at the time of measurement. To this end, it is sufficient to make the layer 41 thick enough to block the probe beam from passing through. For example, when the layer is GaAs, the sufficient thickness is 1.0 μm or more.

The mobility and doping concentration of the doped layer 41 of the samples in FIG. 19A and FIG. 19B can be determined by simply combining the following two well-known measurement methods:

(1) The measurement of a Raman-scattering spectrum of the sample is performed to calculate a carrier density from an observed plasmon-induced peak position of the Raman band. Since carriers are generated by ionizing a dopant, the carrier density obtained corresponds to the ionized dopant density (doping concentration).

(2) Using a contactless sheet resistance measuring apparatus, the sheet resistance of the sample is measured. Since the sheet resistances of the updoped layer and the semi-insulating substrate are much higher than the doped layer, the measured value denotes the sheet resistance of the doped layer.

(3) Using carrier density n and mobility μ, the sheet resistance, Rs, is represented by the following equation:

[Eq. 14] (14)

$$R_s = \frac{1}{e\mu nl}$$

where l is the thickness of the doped layer. From this equation, the mobility can be determined.

As discussed above, the doping concentration and mobility can be measured by the known methods in a non-destructive and contactless manner. It means that the sample structures shown in FIGS. 19A and 19B have the advantage of being able to determine the surface recombination velocity and the surface Fermi level precisely.

Finally, a specific example of this invention will be illustrated. FIG. 1 shows PR spectra measured varying power densities of probe beam. The sample used for the measurements has a structure of i-GaAs (200 nm)/n-GaAs (3.0 μm, $3.0 \times 10^{18}$ cm$^{-3}$)/semi-insulating GaAs, where the values in parentheses are the film thickness and doping concentration of each layer.

An oscillation pattern explicitly appears in each spectrum. These oscillation patterns are FK oscillations resulting from respective surface electric fields. The period of FK oscillation observed becomes greater as the probe beam power density is reduced. As shown in Equation (1b), the increase in the period of FK oscillation denotes an increase in the surface electric field strength of the sample.

FIG. 2 shows plots of the extrema of FK oscillations as a function of quasi-index Xj according to Equation (1a) in order to calculate surface electric field strengths from the FK oscillations. The closed circles represent the extrema at the probe beam power density of 30 µW/cm$^2$, and the open circles represent the extrema at the probe beam power density of 5.5 µW/cm$^2$. From these plots, the surface electric field strengths at the probe beam power densities of 30 µW/cm$^2$ and 5.5 µW/cm$^2$ are calculated as 26.0 kV/cm and 28.2 kV/cm, respectively.

Surface electric field strengths under the other probe beam power density conditions are calculated in the same manner. FIG. 4 shows the obtained surface electric field strengths plotted as a function of probe beam power density. The closed circles represent the electric field strengths obtained from the FK oscillations. It is apparent from FIG. 4 that the electric field strength depends on the logarithm of the probe beam power density. This result corresponds to FIG. 9A.

Figure 20:
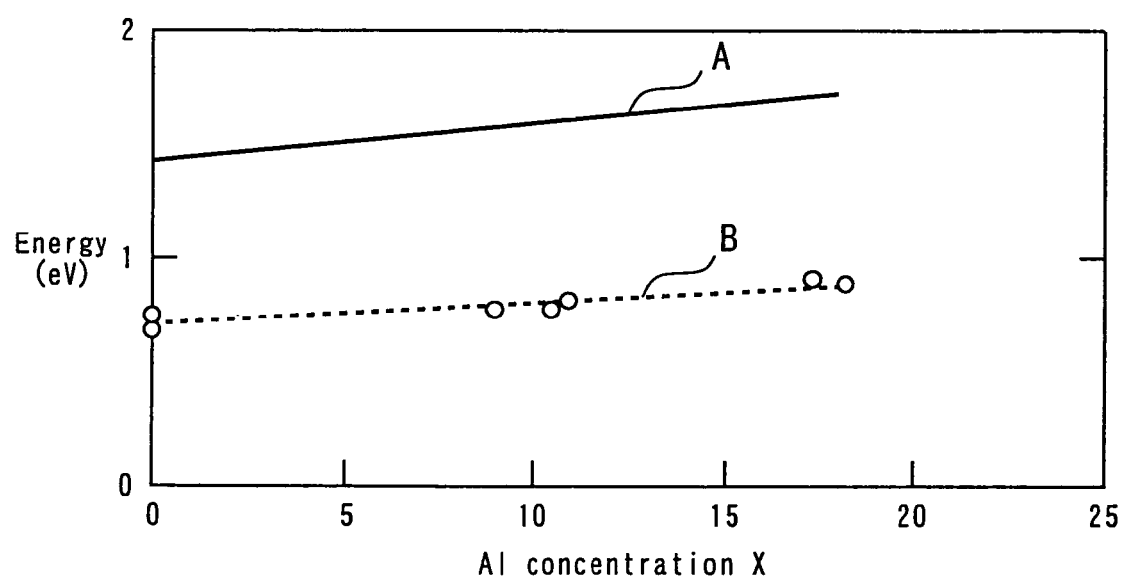
FIG. 20 shows the surface Fermi level in an i-AlGaAs epi layer.

Simulation-fitting is performed to extract the surface Fermi level and the surface recombination velocity from the data. The solid line is the outcome of the simulation-fitting, and the resultant surface Fermi level and surface recombination velocity are ±0.0 eV and $2.0 \times 10^5$ cm/s, respectively. Among these parameters, the surface Fermi level agrees with the published value in FIG. 20 cited from Shen et al., Appl. Phys. Lett. 57, 2118 (1990). FIG. 20 shows the surface Fermi level in an i-AlGaAs epilayer, where the line A represent the bandgap energy and the line B represents the surface Fermi level.

Similarly, the surface recombination velocity is also consistent with the published values shown in Table 3. Table 3, qcited from C. A. Hoffman et al., J. Appl. Phys. 51, 1603 (1980), lists the published values of surface recombination velocities at GaAs surfaces. From these published data, it is concluded that this invention is an effective method for determining the surface Fermi level and the surface recombination velocity at the same time.

TABLE 3

| Sample | Surface Recombination velocity ($\times 10^5$ cm/s) |
| --- | --- |
| n-GaAs (at doping concentration of $6.0 \times 10^{16}$ cm$^{-3}$) | 5 ± 1 |
| n-GaAs (at doping concentration of $1.0 \times 10^{17}$ cm$^{-3}$) | 3 ± 1 |
| p-GaAs (at doping concentration of $1.7 \times 10^{17}$ cm$^{-3}$) | 7 ± 1 |
| GaAs: Cr | 2 ± 1 |

It is further understood that the foregoing description is a preferred embodiment of the disclosed method and apparatus and that various changes and modifications may be made in the invention without departing from the spirit and scope thereof.

The entire disclosure of a Japanese Patent Application No. 2004-316818, filed on Oct. 29, 2004 including specification, claims, drawings and summary, on which the Convention priority of the present application is based, are incorporated herein by reference in its entirety.

What is claimed is:

1. A measurement apparatus for measuring surface carrier recombination velocity, comprising:

a light modulator;

an excitation light source for irradiating a surface of a semiconductor sample with a pump beam via the light modulator;

a probe light source for irradiating the surface of the semiconductor sample with a probe beam;

an instrument for maintaining surface temperature of the semiconductor sample constant while irradiating the surface of the semiconductor sample with the probe beam and the pump beam;

a first light detector for spectrally detecting probe beam light that is reflected from the surface of the semiconductor sample;

a second light detector for detecting photoluminescence of the semiconductor sample and light scattered from the surface of the semiconductor sample while the semiconductor sample is irradiated by at least one of the probe beam and the pump beam;

a differential amplifier for comparing a first signal corresponding to surface electric field strength of the semiconductor sample and produced by the first light detector and a second signal corresponding to photoluminescence of the semiconductor sample and scattered light scattered from the surface of the semiconductor sample and produced by the second light detector; and a calculator for calculating the surface electric field strength from the period of Franz-Kleldysh oscillations appearing in an output signal produced by the differential amplifier.

2. A method of measuring surface carrier recombination velocity and surface Fermi level of a semiconductor sample, the method comprising:

maintaining a semiconductor at a constant temperature while irradiating a surface of the semiconductor sample with a pump beam and while irradiating the surface of the semiconductor sample with a probe beam;

measuring a light-modulated spectrum of the probe beam reflected from the surface of the semiconductor sample;

calculating a surface electric field strength from the period of Franz-Keldysh oscillations appearing in the light-modulated spectrum; and calculating the surface recombination velocity and surface Fermi level from the surface electric field strength and power density of the probe beam.

3. The method according to claim 2, including using contactless electric-field modulation spectroscopy to evaluate the surface recombination velocity and the surface Fermi level at the same time.

4. The method according to claim 2, wherein the semiconductor sample is composed of stacked layers of a high-resistivity or semi-insulating substrate, an n- or p-type semiconductor layer, and a high-resistivity or undoped layer.

* * * * *